United States Patent
Barelle et al.

(10) Patent No.: US 11,692,025 B2
(45) Date of Patent: *Jul. 4, 2023

(54) SINGLE DOMAIN BINDING MOLECULE

(71) Applicant: ELASMOGEN LIMITED, Aberdeen (GB)

(72) Inventors: Caroline Barelle, Aberdeen (GB); Mischa Roland Muller, Zurich-Schlieren (CH); Valerie Calabro, Carro (FR); Jack Bikker, Union Beach, NJ (US); John Steven, Aberdeen (GB); Lioudmila Tchistiakova, Cambridge, MA (US); Oleg Kovalenko, Cambridge, MA (US); Andrea Olland, Arlington, MA (US)

(73) Assignee: ELASMOGEN LIMITED, Aberdeen (GB)

( * ) Notice: Subject to any disclaimer, the term of this patent is extended or adjusted under 35 U.S.C. 154(b) by 229 days.

This patent is subject to a terminal disclaimer.

(21) Appl. No.: 17/322,139

(22) Filed: May 17, 2021

(65) Prior Publication Data

US 2021/0332116 A1 Oct. 28, 2021

Related U.S. Application Data

(63) Continuation of application No. 16/297,544, filed on Mar. 8, 2019, now Pat. No. 11,034,756, which is a continuation of application No. 15/273,197, filed on Sep. 22, 2016, now Pat. No. 10,287,341, which is a continuation of application No. 15/005,463, filed on Jan. 25, 2016, now Pat. No. 9,475,870, which is a continuation of application No. 13/889,134, filed on May 7, 2013, now abandoned.

(60) Provisional application No. 61/643,407, filed on May 7, 2012.

(51) Int. Cl.
| | | |
|---|---|---|
| C07K 16/18 | (2006.01) | |
| C07K 16/28 | (2006.01) | |
| C07K 16/46 | (2006.01) | |
| A61K 39/00 | (2006.01) | |

(52) U.S. Cl.
CPC .......... *C07K 16/18* (2013.01); *C07K 16/2827* (2013.01); *C07K 16/46* (2013.01); *A61K 2039/505* (2013.01); *C07K 2317/24* (2013.01); *C07K 2317/31* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | |
|---|---|---|
| 7,977,071 B2 | 7/2011 | Nuttal et al. |
| 9,475,870 B2 | 10/2016 | Barelle' |
| 2012/0000321 A1 | 1/2012 | Nuttall |
| 2016/0068600 A1 | 3/2016 | Barelle et al. |
| 2016/0176951 A1 | 6/2016 | Barelle et al. |

FOREIGN PATENT DOCUMENTS

| | | | |
|---|---|---|---|
| EP | 2281837 A2 | 8/2002 | |
| EP | 2202243 A2 | 6/2010 | |
| EP | 2277913 A2 | 1/2011 | |
| EP | 2277914 A2 | 1/2011 | |
| WO | 03014161 A2 | 2/2003 | |
| WO | 2005118629 A1 | 12/2005 | |
| WO | 2006122786 A2 | 11/2006 | |
| WO | 2006122787 A2 | 11/2006 | |
| WO | 2008028977 A2 | 9/2007 | |
| WO | 2008043821 A1 | 4/2008 | |
| WO | 2008096158 A2 | 8/2008 | |
| WO | 2009/026638 A1 | 3/2009 | |
| WO | 2012073048 A2 | 6/2012 | |
| WO | 2013/167883 A1 | 11/2013 | |
| WO | 2013167883 A1 | 11/2013 | |
| WO | WO-2013167883 A1 * | 11/2013 | ............. C07K 16/18 |

OTHER PUBLICATIONS

Kovalenko et al. "Atypical Antigen Recognition Mode of a Shark Immunoglobulin New Antigen Receptor (IgNAR) Variable Domain Characterized by Humanization and Structural Analysis" J. Biol. Chem. 288:17408-17419. (Year: 2013).*
Alt, Margitta, et al., FEBS Letters, vol. 454, pp. 90-94 (1999).
Coppieters, Ken, et al., Arthritis & Rheumatism, vol. 54, No. 6, pp. 1856-1866 (2006).
Dennis, Mark S., et al., The Journal of Biological Chemistry, vol. 277, No. 38, pp. 35035-35043 (2002).
Dooley, Helen, et al., Molecular Immunology, vol. 40, pp. 25-33 (2003).
Dooley, Helen, et al., PNAS USA, vol. 103, No. 6, pp. 1846-1851 (2006).
Fiehn, C. et al., Rheumatology, vol. 43, pp. 1097-1105 (2004).
Greenberg, Andrew S., Nature, vol. 374, pp. 168-173 (1995).
Holt, Lucy J., et al., Protein Engineering, Design & Selection, vol. 21, No. 5, pp. 283-288 (2008).

(Continued)

*Primary Examiner* — Sudhakar Katakam
*Assistant Examiner* — Zachary J Miknis
(74) *Attorney, Agent, or Firm* — Arrigo, Lee, Guttman & Mouta-Bellum LLP

(57) ABSTRACT

The present invention provides a single domain specific binding molecule having the structure FW1-CDR1-FW2-HV2-FW3a-HV4-FW3b-CDR3-FW4 in which the Framework Regions FW1, FW2, FW3a, FW3b, and FW4, the Complementarity Determining Regions CDR1 and CDR3, and the Hypervariable Regions HV2, and HV4 have amino acid sequences as defined which provide a high affinity anti-human serum albumin (HSA) binding domain.

34 Claims, 13 Drawing Sheets

Specification includes a Sequence Listing.

(56) References Cited

OTHER PUBLICATIONS

Kovalenko, Oleg V, et al., The Journal of Biological Chemistry, vol. 288, No. 24, pp. 17408-17419 (2013).
Muller, Dafne, et. al., The Journal of Biological Chemistry, vol. 282, No. 17, pp. 12650-12660 (2007).
Muller, Mischa et al., mAbs, vol. 4, No. 6, pp. 673-685 (2012).
Nguyen, Allen, et al., Protein Engineering, Design & Selection. vol. 19, No. 7, pp. 291-297 (2006).
Nuttal, Stewart D., et al., Molecular Immunology, vol. 38, pp. 313-326 (2001).
Pedley, R.B., et al., Br. J. Cancer, vol. 70, pp. 1136-31 (1994).
Smith, Bryan J., el. al., Bioconjugate Chem., vol. 12, pp. 750-756 (2001).
Stork, Roland, Protein Engineering, Design & Selection, vol. 20, No. 11, pp. 569-576 (2007).
Stork, Roland, The Journal of Biological Chemistry, vol. 283, No. 12,, pp. 7804-7812 (2008).
Wunder, Andreas, et. al., Int. J. Cancer, vol. 76, pp. 884-890 (1998).
Wunder, Andreas, et. al., J Immunol., vol. 170, pp. 4793-4801 (2003).
Fennell, B.J. et al., J. Mol. Biol., vol. 400, pp. 155-170 (2010).
Stanfield, R.L. et al., Sciene, vol. 305, pp. 1770-1773 (2004).
The International Search Report and Written Opinion for International Application No. PCT/GB2013/051183.
Henderson et al., "Structure of an IgNAR-AMA1 Complex: Targeting a Conserved Hydrophobic Cleft Broadens Malaria Strain Recognition," Structure, vol. 15, pp. 1452-1466, (2007).
Kovalenko et al. "Atypical Antigen Recognition Mode of a Shark Immunoglobulin New Antigen Receptor (IgNAR) Variable Domain Characterized by Humanization and Structural Analysis" J. Biol. Chem. 288: 17408-17419 (2013).
Chames P and Baty D. "Chapter 6 Bispecific Single Domain Antibodies" Bispecific Antibodies, Ed. R.E. Kontermann. p. 101-114 (2011).

\* cited by examiner

```
P2_A03  ARVDQTPRTATKETGESLTINCVLTDTSYPLYSTYWYRKNPGSSNKEQISISGRYVESVNKGTKSFSLRIKDLTVADSATYICRAMGTDSWTGDGAGTVLTVN
P2_C06  IRVDQTPRTATKETGESLTINCVLTDTSYPLYSTYWYRKNPGSSNKEQISISGRYVESVNKGTKSFSLRIKDLTVADSATYICRAMGTNIWTGDGAGTVLTVN
P2_E06  TRVDQTPRTATKETGESLTINCVLTDTSYPLYSTYWYRKNPGSSNKEQISISGRYVESVNKGTKSFSLRIKDLTVADSATYICRAMGTNSWTGDGAGTALTVN
P2_H08  ARVDQTPRTATKETGESLTINCVLTDTSYPLYSTYWYRKNPGSSNKEQISISGRYVESVNKGTKSFSLRIKDLTVADSATYICRAMGTNIWTGDGAGTALTVN
P3_A03  TRVDQTPRTATKETGESLTINCVLTDTSYPLYSTYWYRKNPGSSNKERISISGRYVESVNKGTKSFSLRIKDLTVADSATYICRAMGTBSWTGDGAGTVLTVN
P3_A08  TRVDQTPRTATKETGESLTINCVLTDTSYPLYRTYWYRKNPGSSNKEQISISGRYVESVNKGTKSFSLRIKDLTVADSATYICRAMGTDSWTGDGAGTVLTVN
P3_A12  TRVDQTPRTATKETGESLTINCVLTDTSYPLYSTYWYRKNPGSSNKERISISGRYVESVNKGTKSFSLRIKDLTVADSATYICRAMGTNSWTGDGAGTALTVN
P3_B08  TRVDQTPRTATKETGESLTINCVLTDTSYPLYSTYWYRKNPGSSNKERISISGRYVESVNKGTKSFSLRIKDLTVADSATYICRAMGTNIWTGDGAGTVLTVN
P3_B09  TRVDQTPRTATKETGESLTINCVLTDTSYPLYRTYWYRKNPGSSNKEQISISGRYVESVNKGTKSFSLRIKDLTVADSATYICRAMGTNSWTGDGAGTVLTVN
P3_D03  TRVDQTPRTATKETGESLTINCVLTDTSYPLYSTYWYRKNPGSSNKEQISISGRYVESVNKGTKSFSLRIKDLTVADSATYICRAMGTDSWTGDGAGTALTVN
P3_D05  TRVDQTPRTATKETGESLTINCVLTDTSYPLYSTYWYRKNPGSSNKERISISGRYVESVNKGTKSFSLRIKDLTVADSATYICRAMGTNIWTGDGAGTVLTVN
P3_D10  TRVDQTPRTATKETGESLTINCVLTDTSYPLYSTYWYRKNPGSSNKERISISGRYVESVNKGTKSFSLRIKDLTVADSATYICRAMGTNIWTGDGAGTVLTVN
P3_D11  TRVDQTPRTATKETGESLTINCVLTDTSYPLYSTYWYRKNPGSSNKEQISISGRYVESVNKGTKSFSLRIKDLTVADSATYICRAMGTNIWTGDGAGTVLTVN
P3_E06  TRVDQTPRTATRETGESLTINCVLTDTSYPLYSTYWYRKNPGSSNKEQISISGRYVESVNKGTKSFSLRIKDLTVADSATYICRAMGTNIWTGDGAGTVLTVN
P3_E07  ASVNQTPRTATKETGESLTINCVLTDTSYPLYSTYWYRKNPGSSNKEQISISGRYVESVNKGTKSFSLRIKDLTVADSATYICRAMGTNIWTGDGAGTVLTVN
P3_F03  ASVNQTPRTATKETGESLTINCVLTDTSYPLYSTYWYRKNPGSSNKEQISISGRYVESVNKGTKSFSLRIKDLTVADSATYICRAMDTSAGVVDGAGTVLTVN
P3_F11  AKVDQTPRTATKETGESLTINCVLTDTSYPLYSTYWYRKNPGSSNKEQISISGRYVESVNKGTKSFSLRIKDLTVADSATYICRAMGTDSWTGDGAGTVLTVN
P3_G10  ASVNQTPRTATKETGESLTINCVLTDTSYPLYSTYWYRKNPGSSNKERISISGRYVESVNKGTKSFSLRIKDLTVADSATYICRAMGTDSWTGDGAGTVLTVN
```

TRVDQTPRTATRETGESLTINCVLTDTSYPLYSTYWYRKNPGSSNKEQISISGRYVESVNKGTKSFSLRIKDLTVADSATYICRAMGTNIWTGDGAGTVLTVN (ii)

E06  TRVDQTPRTATRETGESLTINCVLTDTSYPLYSTYWYRKNPGSSNKEQISISGRYVESVNKGTKSFSLRIKDLTVADSATYICRAMGTNIWTGDGAGTVLTVN

BB11 TRVDQSPSSLSASVGDRVTITCVLTDTSYPLYSTYWYRKNPGSSNKEQISISGRYSESVNKGTKSFTLTISSLQPEDFATYYCRAMATNIWTGDGAGTKVEIK

(iii) E06-AAA-6xHis

TRVDQTPRTATRETGESLTINCVLTDTSYPLYSTYWYRKNPGSSNKEQISISGRYVESVNKGTKSFSLRIKDLTVADSATYICRAMGTNIWTGDGAGTVLTVNAAAHHHHHH

FIG. 1(b)

```
P0_02_B12  IRVDQTPRTATKETGESLTINCVLTGTVCGMYSTSWSRKNPGRADWERISIGGRYVESVNKGAKSFSLRIRDLTVADSATYCCSAESPPICTSQGIAAVTK-YYDGAGTVLTVN
P0_05_E09  ARVDQTPRTATKETGESLTINCVLTDTSYPLYSTYWYRKNPGSSNKEQISISGRYVESVNKGTKSFSLRIKDLTVADSATYICRAITTD------SWTS---DGAGTALTVN
P1_09_C07  ARVDQTPRTATKETGESLTINCVLTDTSYPLYSTYWYRKNPGSSNKEQISISGRYVESVNKGTKSFSLRIKDLTVADSATYICRAYTIHI------KLEX---HGAGTVLTVN
P1_08_E06  ARVDQTPRTATKETGESLTINCVLTDTSYPLYSTYWYRKNPGSPNKERISISGRYVESVNKGTKSFSLRIKDLTVADSATYICRAMGAN------SWTG---DGAGTALTVN
P1_07_B06  ASVNQTPRTATKETGESLTINCVLTDASYPLYSTYWYRKNPGSSNKEQIPISGRYVESVNKGTKSFSLRIKDLTVADSATYICRAMGTN------GWTG---DGAGTVLTVN
P1_10_A01  AKVDQTPRTTKETGESLTINCVLTETSYGLSSTSWFQKNPGTTDWERMSIGGRYVESVNTGAKSFSLRIKDLTVADSATYCKAHAGYGVWNRGLQWRGYDXYDGAGTVLTVN
P1_07_G11  TRVDQTPRTATKETGESLTINCVLTDTSYPLYSTYWYRKNPGSSNKEQISISGRYVESVNKGTKSFSLRIKDLTVADSATYICRAYTP------GRED---YGAGTVLTVN
P1_10_D05  ARVDQTPRTATKETGESLTINCVLADTSYPLYSTYWYRKNPGSSNKEQISISGRYVESVNKGTKSFSLRIKDLTVADSATYICRASDIA------MGTY---DGAGTALTVN
P1_09_C11  ASVNQTPRTATKETGESLTINCVLTGTCSLYSTYWFRKNPGTTDWERISIGGRYVESVNKGAKSFSLRIKDLTVADSATYCCKAEKG-RKGSAITSCRRSSYYDGAGTVLTVN
P1_10_A02  ARVDQTPRTATKETGESLTINCVLTDTSYPLYSTYWYRKNPGSSNKEQISISGRYVESVNKGTKSFSLRIKDLTVADSGTYICRSITTH------SWSG---DGAGTALTVN
P1_10_C03  IRVDQTPRTATKETIGGSLTINCVLTDTSYPLYSTYWYRKNPGSSNKEQISISGRYVESVNKGTKSFSLRIKDLTVADSATYICRALSTY------MEAG---DGAGTVLTVN
P1_10_C11  ASVNQTPRTATKETGESLTINCVLTDTSYPLYSTYWYRKNPGSSNKEQIPISGRYVESVNKGTKSFSLRIKDLTVADSATYICRAMDTS------AGVV----DGAGTVLTVN
Naive 2V   TRVDQTPRTATKETGESLTINCVLTDTSYGLYSTYWFRKNPGTTDWERMSIGGRYVESVNKGAKSFSLRIKDLTVADSATYYCKAQS------LAISTRSY-WYDGAGTVLTVN
``` where X represents Q

FIG. 1(c)

| | CDR1 | | CDR2 | | CDR3 | |
|---|---|---|---|---|---|---|
DPK-9      DIQMTQSPSSLSASVGDRVTITC..RASQSISSYLNWYQQKPGK.APKLLIYAASSLQSGVPSRFSGSGSG...TDFTLTISSLQPEDFATYYC............QQSYSAPRTFGQGTKVEIK
5A7        ARVDQTPRSVTKETGESLTINCVLRDASYALGSTCWYRKKSGEGNEESISKG.........GRYVETVNSGSKSFSLRINDLTVEDGGTYRCLGVAGGYCDYALCSSRYAECGDGTAVTVN
5A7-IVabc  ARVDQSPSSLSASVGDRVTITCVLRDASYALGSTCWYRKKSGEGNEESISKG.........GRYSESVNSGSKSFTLTISSLQPEDFATYYCLGVAGGYCDYALCSSRYAECGQGTKVEIK
E06        TRVDQTPRIATRETGESLTINCVLTDTSYPLYSTYWYRKNPGSSNKEQISIS.........GRYVESVNKGTKSFSLRIKDLTVADSATYICRA.............MGTNIWTGDGAGTVLTVN
huE06-v1.1 TRVDQSPSSLSASVGDRVTITCVLTDTSYPLYSTYWYQQKPGSSNKEQISIS.........GRYSESVNKGTKSFTLTISSLQPEDFATYYCRA.............MGTNIWTGDGAGTKVEIK
huE06-v1.2 TRVDQSPSSLSASVGDRVTITCVLTDTSYPLYSTYWYQQKPGSSNKEQISIS.........GRYSESVNSGSKSFTLTISSLQPEDFATYYCRA.............MGTNIWTGDGAGTKVEIK
huE06-v1.3 TRVDQSPSSLSASVGDRVTITCVLTDTSYPLYSTYWYQQKPGK.APKQISIS.........GRYSESVNSGSKSFTLTISSLQPEDFATYYCRA.............MGTNIWTGDGAGTKVEIK
huE06-v1.4 DIQMTQSPSSLSASVGDRVTITCVLTDTSYPLYSTYWYQQKPGK.APKQISIS.........GRYSESVNSGSKSFTLTISSLQPEDFATYYCRA.............MGTNIWTGDGAGTKVEIK
huE06-v1.5 TRVDQSPSSLSASVGDRVTITCVLTDTSYPLYSTYWYQQKPGKQAPKLLQISIS........GRFSESGSG..TDFTLTISSLQPEDFATYYCRA.............MGTNIWTGDGAGTKVEIK
huE06-v1.7 TRVDQSPSSLSASVGDRVTITCVLTDTSYPLYSTYWYQQKPGK.APKQISIS.........GRYSESVNKGTKSFTLTISSLQPEDFATYYCRA.............MGTNIWTGDGAGTKVEIK
huE06-v1.10 TRVDQSPSSLSASVGDRVTITCVLTDTSYPLYSTYWYRKNPGSSNKEQISIS.........GRYSESVNKGTKSFTLTISSLQPEDFATYYCRA.............MGTNIWTGDGAGTKVEIK FW1  CDR1  FW2  HV2  FW3a  HV4  FW3b  CDR3  FW4

FIG. 2(a)

```
i) 5A7-IVabc
ARVDQSPSSLSASVGDRVTITCVLRDASYALGSTCWYQQKPGKAPKSISKGGRYSESVNSGSKSFTLTISSLQPEDFATYYCGLGVAGGYCDYALCSSRYAECGQGTKVEIK ii) huE06 v1.1
TRVDQSPSSLSASVGDRVTITCVLTDTSYPLYSTYWYQQKPGSSNKEQISISGRYSESVNKGTKSFTLTISSLQPEDFATYYCRAMGTNIWTGDGAGTKVEIK iii) huH08 v1.1
ARVDQSPSSLSASVGDRVTITCVLTDTSYPLYSTYWYQQKPGSSNKEQISISGRYSESVNKGTKSFTLTISSLQPEDFATYYCRAMGTNIWTGDGAGTALTVN iv) huE06 v1.2
TRVDQSPSSLSASVGDRVTITCVLTDTSYPLYSTYWYQQKPGSSNKEQISISGRYSESVNSGSKSFTLTISSLQPEDFATYYCRAMGTNIWTGDGAGTKVEIK v) huE06 v1.3
TRVDQSPSSLSASVGDRVTITCVLTDTSYPLYSTYWYQQKPGKAPKQISISGRYSESVNSGSKSFTLTISSLQPEDFATYYCRAMGTNIWTGDGAGTKVEIK vi) huE06 v1.4
DIQMTQSPSSLSASVGDRVTITCVLTDTSYPLYSTYWYQQKPGKAPKQISISGRYSESVNKGTKSFTLTISSLQPEDFATYYCRAMGTNIWTGDGAGTKVEIK vii) huE06 v1.5
TRVDQSPSSLSASVGDRVTITCVLTDTSYPLYSTYWYQQKPGKAPKLQISISGRFSESGSGTDFTLTISSLQPEDFATYYCRAMGTNIWTGDGAGTKVEIK viii) huE06 v1.6
TRVDQSPSSLSASVGDRVTITCVLTDTSYPLYSTYWYQQKPGKAPKLLIYAASSLQSGVPSRFSGSGSGTDFTLTISSLQPEDFATYYCRAMGTNIWTGDGAGTKVEIK ix) huE06 v1.7
TRVDQSPSSLSASVGDRVTITCVLTDTSYPLYSTYWYQQKPGKAPKQISISGRYSESVNKGTKSFTLTISSLQPEDFATYYCRAMGTNIWTGDGAGTKVEIK x) huE06 v1.8
TRVDQSPSSLSASVGDRVTITCVLTDTSYPLYSTYWYRKNPGSSNKEQISISGRYSESVNKGTKSFTLTIKSLQPEDFATYICRAMGTNIWTGDGQGTKVEIK xi) huE06 v1.9
TRVDQSPSSLSASVGDRVTITCVLTDTSYPLYSTYWYRKNPGSSNKEQISISGRYSESGSGTDFTLTIKSLQPEDFATYICRAMGTNIWTGDGQGTKVEIK xii) huE06 v1.10
TRVDQSPSSLSASVGDRVTITCVLTDTSYPLYSTYWYRKNPGSSNKEQISISGRYSESVNKGTKSFTLTISSLQPEDFATYICRAMGTNIWTGDGAGTKVEIK
```

FIG. 2(b)

```
E06       TRVDQTPRTATRETCGESLTINCVLTDTSYPLYSTYWYRKNPGSSNKEQISISGRYVESVNKGTKSFSLRIKDLTVADSATYICRAMGTNIWTGDGAGTVLTVN
hE06v1.10 TRVDQSPSSLSASVGDRVTITCVLTDTSYPLYSTYWYRKNPGSSNKEQISISGRYSESVNKGTKSFTLTISSLQPEDFATYYCRAMGTNIWTGDGAGTKVEIK
AC9       TRVDQSPSSLSASVGDRVTITCVLTDTSYPLYSTYWYRKNPGSSNKEQISISGRYSESVNKSTLTISSLQPEDFATYYCRAMGTNIWTGDGAGTKVEIK
AD4       TRVDQSPSSLSASVGDRVTITCVLTDTSYPLYSTYWYRKNPGSSNKEQISMSGRYSESVNKSTKSFTLTISSLQPEDFATYYCRAMGTNIWTGDGAGTKVEIK
AG11      TRVDQSPSSLSASVGDRVTITCVLTDTSYPLYSTYWYRKNPGSSNKEQISISGRYSESVNKGTKSFTLTISSLQPEDFATYYCRAMGTNIWTGDGAGTKVETK
AH7       TRVDQTPSSLSASVGDRVTITCVLTDTSYPLYSTYWYRKNPGSSNKEQISISGRYSESVNKGTKSFTLTISSLQPEDSATYYCRAMGTNIWTGDGAGTKVEIK
BA11      TRVDQSPSSLSASVGDRVTITCVLTDTSYPLYSTYWYRKNPGSSNKEQISISGRYSESVNKGTKSFTLTISSLQPEDFATYYCRAMSTNIWTGDGAGTKVEIK
BB10      TRVDQSPSSLSASVGDRVTITCVLTDTSYPLYSTYWYRKNPGSSNKEQISISGRYSESVNKGTKSFTLTISSLQPEDFATYYCRAMGTNFWTGDGAGTKVEIK
BB11      TRVDQSPSSLSASVGDRVTITCVLTDTSYPLYSTYWYRKNPGSSNKEQISISGRYSESVNKGTKSFTLTISSLQPEDFATYYCRAMATNIWTGDGAGTKVEIK
BC3       TRVDQSPSSLSASVGDRVTITCVLTDTSYPLYSTYWYRKNPGSNNKEQISISGRYSESVNKGTNSFTLTISSLQPEDFATYYCRAMGTNIWTGDGAGTKVEIK
BD12      TRVDQSPSSLSASVGDRVTITCVLTDTSYPLYSTYWYRKNPGSSNKEQISISGRYSESVNKGTKSFTLTISSLQPEDFATYYCRAMGTNIWTGDGAGTKVEIK
BE4       TRVDQSPSSLSASVGDRVTITCVLTDTSYSLYSTYWYRKNPGSSNKEQISISGRYSESVNKGTKSFTLTISSLQPEDFATYYCRAMGTNIWTGDGAGTKVEIK
BH4       TRVDQSPSSLSASVGDRVTITCVLTDTSYPLYSTYWYRKNPGSSNKEQISISGRYSESVNKGTKSFTLTISSLQPEDFATYYCRAMGTNLWTGDGAGTKVEIK
```

FIG. 2(c)

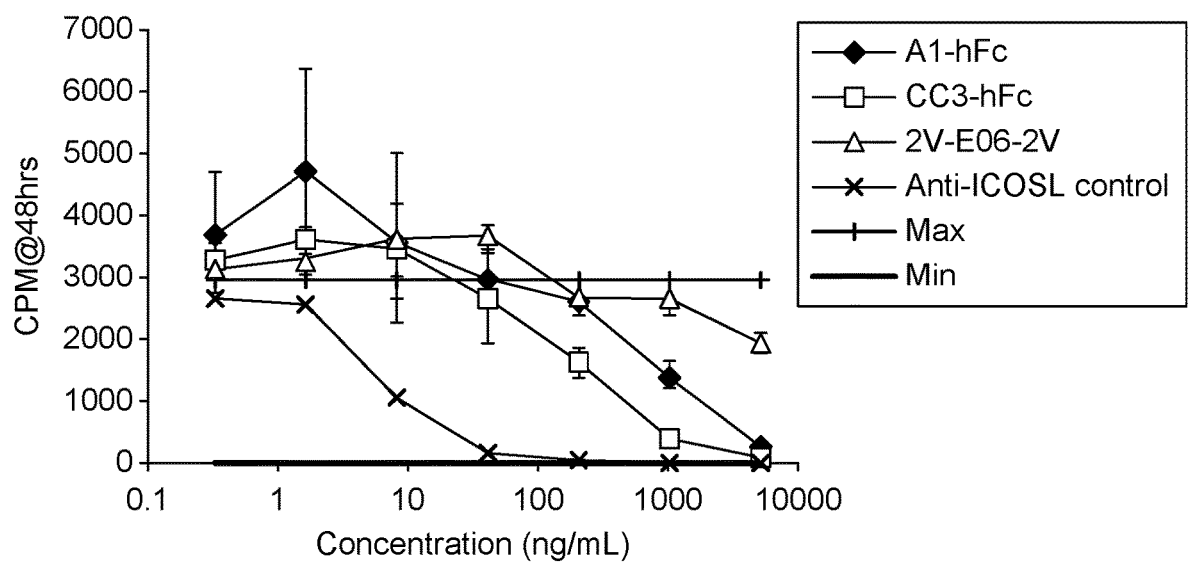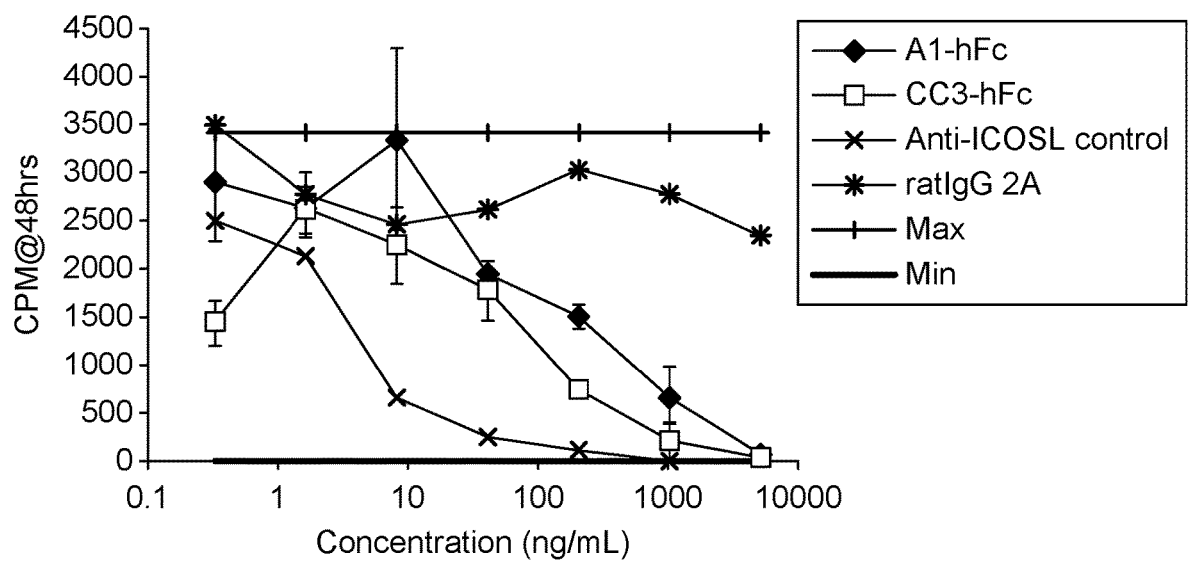
FIG. 5(b)

SINGLE DOMAIN BINDING MOLECULE

The present invention relates to a single domain specific binding molecule derived from an antigen binding protein from cartilaginous fish.

Novel antigen receptor (IgNAR) is a single heavy chain binding domain, devoid of light chain, that exists in the sera of cartilaginous fish (Greenberg et al, *Nature,* 374 168-173 (1995)). The IgNARs are therefore a class of immunoglobulin-like molecules of the shark immune system that exist as heavy-chain-only homodimers and bind antigens by their single variable domains (VNARs). The distinct structural features of VNARs are the lack of hydrophobic VH/VL interface residues and the truncation of CDR2 loop present in conventional immunoglobulin variable domains.

Following shark immunization and/or in vitro selection, VNARs can be generated as soluble, stable and specific high-affinity monomeric binding proteins of approximately 12 kDa that are amenable to classic phage display selection and screening making them attractive candidates for biotherapeutic development (WO 03/014161).

Recent developments in the field of medicine have identified many antibodies with potentially useful therapeutic applications. However, there are limitations in the current format of these proteins; antibodies being structurally complex multi-domain molecules are relatively large globular proteins that restrict accessibility to extra-cellular and recessed more cryptic targets. Accordingly, it has been a goal to develop smaller, more stable, specific binding domains which can be achieved through reducing the size of the antibody to the binding domain itself, variations thereof (e.g. scFv, Fab', Fab, sdAb) or seeking novel scaffolds upon which to engineer target selectivity and affinity. The challenge in such approaches being that the smaller the domain, the more rapid its clearance which may be advantageous for diagnostic imaging, but is far from optimal for the treatment or management of chronic disease. Tailoring the half-life of therapeutic drugs would negate the requirement for multiple administrations hence minimizing accumulative damage to the patient, increasing patient compliance and reducing the overall dosing regime which, from a commercial perspective, greatly reduces costs.

Naturally occurring single domain antibodies offer the opportunity to reduce the minimal binding domain further through their inherent lack of light chain partner. Convergent evolution has resulted in two very diverse classes of animal developing such domains as an integral part of their immune repertoire; the IgNARs from cartilaginous fish and the VHHs or nanobodies from the camelidae (camels, dromedaries and llamas) that bring great pharmaceutical promise through their stability, solubility and unique binding loop topography. However with an average molecular mass of 12 to 13 kDa, they are subsequently rapidly cleared in vivo by glomerular filtration.

Significant efforts to address the question of systemic half-life extension have included different strategies to counter unfavourable pharmacokinetic properties. Increasing the size of the antibody domain to prevent glomerular clearance has been achieved by increasing the hydrodynamic size via chemical modification of random or directed conjugation to polyethylene glycol (PEG). Other re-formatting strategies such as alterations to site-specific glycosylation have shown moderately increased plasma half-life whilst exploitation of the FcRn re-cycling system by molecular Fc fusions have significantly extended circulating antibody fragment concentration (Pedley et al, *British Journal of Cancer* 70(6), 1126-1130 (1994), Stork et al, *The Journal of Biological Chemistry* 283(12), 7804-7812 (2008), Alt et al, *FEBS Letters* 454(1-2), 90-94 (1999)).

Another strategy that hijacks this natural recycling system is the use of serum albumin binding to extend the circulating half-life of smaller proteins or peptides. Albumin is a large (~67 kDa), abundant serum protein that plays multiple biological roles in the body such as osmotic haemostasis, fatty acid, lipid and metabolite transfer, metal ion binding and drug elimination. It has been shown to distribute to regions of inflammation as illustrated in animal models of arthritis (Fiehn et al, *Rheumatology,* 43(9), 1097-1105 (2004); Wunder et al, *J. Immunol* 170(9), 4793-4801 (2003)) and to accumulate in proliferating environments such as tumour stroma (Wunder et al, *International Journal of Cancer* 76(6), 884-890 (1998)).

With a half-life of approximately 19 days in humans, its relative abundance and unique disease-related distribution profile, serum albumin has been a target and tool for half-life extension of short-lived smaller proteins and peptide. This has been achieved through multiple methods such as chemical linking, association through acylation, molecular fusions and fusion to bacterial albumin binding domains (Smith et al, *Bioconjugate Chemistry* 12(5), 750-756 (2001), Muller et al, *The Journal of Biological Chemistry,* 282(17), 12650-12660 (2007), Stork et al, *Protein Eng Des Sel,* 20(11), 546-576 (2007)). Peptide display has yielded multiple different short amino acid sequences that bind with varying affinities to different albumin species and when fused to antibody fragments, can both increase their half-life and improve biodistribution (Dennis et al, *JBC* 277(38), 35035-35043 (2002); Nguyen et al, *Protein Eng Des Sel* 19(7), 291-297 (2006).). Another protein based strategy has been to raise or isolate domain antibodies (dAbs) and camelid VHH binding domains (nanobodies) against albumin and fuse these to create albumin binding constructs (Holt et al, *Protein Eng Des Sel* 21(5), 283-288 (2008); Coppieters et al, *Arthritis and Rheumatism* 54(6), 1856-1866 (2006)).

However, there is a continuing need to provide therapeutics with an improved half-life that are active at lower plasma concentrations to avoid the potential for unwanted side-effects at higher dosages. For such therapeutic agents based on immunoglobulin proteins, there is a further need to provide humanised forms that retain activity.

It has now been found that a particular Variable domain (VNAR) of shark novel antigen receptor (IgNAR) can provide a high affinity anti-human serum albumin (HSA) VNAR binding domain. Unusually for this type of domain, the interacting residues are not solely within the CDR or HV regions but also include framework residues. The isolation of this anti-HSA VNAR has significant utility as demonstrated by in vivo efficacy in increasing the sera half-life of a fused unrelated VNAR binding domain. The present invention therefore provides the means for developing bi- or multi-valent therapeutically relevant constructs with extended sera half-life through fusion with the anti-HSA VNAR domain.

According to a first aspect of the invention there is provided a single domain specific binding molecule having the structure FW1-CDR1-FW2-HV2-FW3a-HV4-FW3b-CDR3-FW4 in which the Framework Regions FW1, FW2, FW3a, FW3b, and FW4, the Complementarity Determining Regions CDR1 and CDR3, and the Hypervariable Regions HV2, and HV4 have amino acid sequences in which FW1 comprises TRVDQTPRTATRETGESLTINCVLT (SEQ ID NO: 1),
FW2 comprises TYWYRKNPGS (SEQ ID NO: 2),
FW3a comprises GRYVESVN (SEQ ID NO: 3),
FW3b comprises FSLRIKDLTVADSATYICRA (SEQ ID NO: 4),
FW4 comprises GAGTVLTVN (SEQ ID NO: 5),
CDR1 comprises DTSYPLYS (SEQ ID NO: 6),
CDR3 comprises
(i) MGTNIWTGD (SEQ ID NO: 7),
(ii) MATNIWTGD (SEQ ID NO: 8), MGTDSWTGD (SEQ ID NO:9), MGTNSWTGD (SEQ ID NO: 10), MSTNIWTGD (SEQ ID NO: 11), ITTDSWTSD (SEQ ID NO: 12), MGANSWTGD (SEQ ID NO: 13), MGTNGWTGD (SEQ ID NO: 14), SDIAMGTYD (SEQ ID NO: 15), ITTHSWSGD (SEQ ID NO: 16), LSTYMEAGD (SEQ ID NO: 17), MDTSAGVVD (SEQ ID NO: 18),
(iii) ESPPICTSQGIAAVTKYYD (SEQ ID NO: 19), YTIHIKLEXH (SEQ ID NO: 20), HAGYGVWNRGLQWRGYDXYD (SEQ ID NO: 21), YTPGREDY (SEQ ID NO: 22), EKGRKGSAITSCRRSSYYD (SEQ ID NO: 23), QSLAISTRSYWYD (SEQ ID NO: 24), or
(iv) GVAGGYCDYALCSSRYAE (SEQ ID NO: 25),
HV2 comprises SNKEQISIS (SEQ ID NO: 26),
HV4 comprises KGTKS (SEQ ID NO: 27),
or a sequence having at least 50% identity thereto, where the amino acid residue "X" represents glutamine (Q).

Preferred sequences of the invention are shown in FIG. 1(b) as E06, BB11 and E06 with a poly-histidine C-terminal sequence (E06-AAA-6×His), or a sequence having at least 50% identity thereto. In a comparison of E06 (SEQ ID NO: 46) and BB11 (SEQ ID NO: 85), there are 28 out of 103 amino acid residues that are different, so the sequences are 27% different and have a degree of homology of 73%.

Where "X" is Q, then sequences YTIHIKLEXH (SEQ ID NO: 20) and HAGYGVWNRGLQWRGYDXYD (SEQ ID NO: 21) are YTIHIKLEQH (SEQ ID NO: 20) and HAGYGVWNRGLQWRGYDQYD (SEQ ID NO: 21) respectively.

The single domain specific binding molecule of the present invention is based on a single variable domain (VNAR) of an IgNAR immunoglobulin-like molecule. The single domain specific binding molecule suitably comprises the following domains:

FW1-CDR1-FW2-HV2-FW3a-HV4-FW3b-CDR3-FW4 in which FW is a Framework Region, CDR is a Complementarity Determining Region, and HV is a Hypervariable Region. In common with other VNAR molecules, there is no CDR2 region as in a mammalian antibody variable (V) domain.

In one embodiment of the invention, there is provided a single domain specific binding molecule having the structure FW1-CDR1-FW2-HV2-FW3a-HV4-FW3b-CDR3-FW4 in which
FW1, FW2, FW3a, FW3b and FW4 are Framework Regions having the amino acid sequences TRVDQTPRTATRETGESLTINCVLT (SEQ ID NO: 1), TYWYRKNPGS (SEQ ID NO: 2), GRYVESVN (SEQ ID NO: 3), FSLRIKDLTVADSATYICRA (SEQ ID NO: 4), and GAGTVLTVN (SEQ ID NO: 5) respectively;
CDR1 and CDR3 are Complementarity Determining Regions having the amino acid sequences DTSYPLYS (SEQ ID NO: 6), and MGTNIWTGD (SEQ ID NO: 7) or GVAGGYCDYALCSSRYAE (SEQ ID NO: 25) respectively;
HV2 and HV4 are Hypervariable Regions having the amino acid sequences SNKEQISIS (SEQ ID NO: 26) and KGTKS (SEQ ID NO: 27) respectively;
or a sequence having at least 50% identity thereto. An example of a single domain specific binding molecule having the specific sequence defined where CDR1 and CDR3 are DTSYPLYS (SEQ ID NO: 6), and MGTNIWTGD (SEQ ID NO: 7) is sequence E06.

In one embodiment of the invention, there is provided a single domain specific binding molecule having the structure FW1-CDR1-FW2-HV2-FW3a-HV4-FW3b-CDR3-FW4 in which
FW1, FW2, FW3a, FW3b and FW4 are Framework Regions having the amino acid sequences
TRVDQSPSSLSASVGDRVTITCVLT (SEQ ID NO: 28), TYWYRKNPGS (SEQ ID NO: 2), GRYSESVN (SEQ ID NO: 30),
FTLTISSLQPEDFATYYCRA (SEQ ID NO: 31) and GAGTKVEIK (SEQ ID NO: 32) respectively
CDR1 and CDR3 are Complementarity Determining Regions having the amino acid sequences DTSYPLYS (SEQ ID NO: 6) and MATNIWTGD (SEQ ID NO: 8) respectively;
HV2 and HV4 are Hypervariable Regions having the amino acid sequences SNKEQISIS (SEQ ID NO: 26) and KGTKS (SEQ ID NO: 27) respectively;
or a sequence having at least 50% identity thereto. The single domain specific binding molecule having the above specific sequence is BB11.

In another embodiment of the invention, the Framework Regions FW1, FW2, FW3a, FW3b and FW4 of the single domain specific binding molecule have the amino acid sequences TRVDQSPSSLSASVGDRVTITCVLT (SEQ ID NO: 28), TYWYQQKPGS (SEQ ID NO: 29), GRYSESVN (SEQ ID NO: 30), FTLTISSLQPEDFATYYCRA (SEQ ID NO: 31) and GAGTKVEIK (SEQ ID NO: 32) respectively.

Specific binding molecules of this aspect of the invention may have sequences as set out in FIG. 1(a): P2_A03, P2_C06, P2_E06, H08, P3_A03, P3_A08, P3_A12, P3_B08, P3_B09, P3_D03, P3_D05, P3_D10, P3_D11, E06, P3_E07, P3_F03, P3_F11, and P3_G10, or a sequence having at least 50% identity thereto.

In another aspect of the invention, the specific binding molecule may have a sequence as shown in FIG. 1(c): P0_02_B12, P0_05_E09, P1_09_C07, P1_08_E06, P1_07_B06, P1_10_A01, P1_07_G11, P1_10_D05, P1_09_C11, P1_10_A02, P1_10_C03, and P1_10_C11, or a sequence having at least 50% identity thereto. The sequences shown in FIG. 1(c) also relate to anti-HSA binding domains isolated from a pre-selected phage display library.

In another aspect of the invention, the specific binding molecule may have a sequence as shown in FIG. 2(a), 2(b) or 2(c), in particular sequences E06, BB11, 5A7, 5A7-IVabc, huE06 v1.1, huH08 v1.1, huE06 v1.2, huE06 v1.3, huE06 v1.4, huE06 v1.5, huE06 v1.6, huE06 v1.7, huE06 v1.8, huE06 v1.9, huE06 v1.10, AC9, AD4, AG11, AH7, BA11, BB10, BC3, BD12, BE4, or BH4, or a sequence having at least 50% identity thereto. The sequences huE06 v1.10 and BB11 therefore share the same framework and differ by one amino acid residue in CDR3.

In one embodiment of this aspect of the invention, the CDR3 region comprises (i) MGTNIWTGD (SEQ ID NO: 7),
(ii) GVAGGYCDYALCSSRYAE (SEQ ID NO: 25),
(iii) ESPPICTSQGIAAVTKYYD (SEQ ID NO: 19), YTIHIKLEXH (SEQ ID NO: 20), HAGYGVWNRGLQWRGYDXYD (SEQ ID NO: 21), YTPGREDY (SEQ ID NO: 22), EKGRKGSAITSCRRSSYYD (SEQ ID NO: 23), QSLAISTRSYWYD (SEQ ID NO: 24), or
(iv) ITTDSWTSD (SEQ ID NO: 12), MGANSWTGD (SEQ ID NO: 13), MGTNGWTGD (SEQ ID NO: 14), SDIAMGTYD (SEQ ID NO: 15), ITTHSWSGD (SEQ ID NO: 16), LSTYMEAGD (SEQ ID NO: 17), MDTSAGVVD (SEQ ID NO: 18), or a sequence having at least 50% identity thereto. The amino acid residue "X" represents glutamine (Q).

The term "protein" in this text means, in general terms, a plurality of amino acid residues joined together by peptide bonds. It is used interchangeably and means the same as peptide, oligopeptide, oligomer or polypeptide, and includes glycoproteins and derivatives thereof. The term "protein" is also intended to include fragments, analogues, variants and derivatives of a protein wherein the fragment, analogue, variant or derivative retains essentially the same biological activity or function as a reference protein. Examples of protein analogues and derivatives include peptide nucleic acids, and DARPins (Designed Ankyrin Repeat Proteins).

The fragment, analogue, variant or derivative of the protein as defined in this text, may be at least 25 preferably 30 or 40, or up to 50 or 100, or 60 to 120 amino acids long, depending on the length of the original protein sequence from which it is derived. A length of 90 to 120, 100 to 110 amino acids may be convenient in some instances.

The fragment, derivative, variant or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the additional amino acids are fused to the mature polypeptide, such as a leader or auxiliary sequence which is employed for purification of the polypeptide. Such fragments, derivatives, variants and analogues are deemed to be within the scope of those skilled in the art from the teachings herein.

In certain preferred embodiments of the invention, the single domain specific binding molecule has an amino acid sequence selected from the group consisting of VNAR domains shown in FIG. 1(a), in which FW1 comprises residues 1 to 25 CDR1 comprises residues 26 to 33, FW2 comprises residues 34 to 43, HV2 comprises residues 44 to 52, FW3a comprises residues 53 to 60, HV4 comprises residues 61 to 65, FW3b comprises residues 66 to 85, CDR3 comprises residues 86 to 94 and FW4 comprises residues 95 to 103, or any combination thereof.

In certain preferred embodiments of the invention, the single domain specific binding molecule has an amino acid sequence selected from the group consisting of VNAR domains shown in FIG. 1(c), in which FW1 comprises residues 1 to 27, CDR1 comprises residues 28 to 33, FW2 comprises residues 34 to 43, HV2 comprises residues 44 to 52, FW3a comprises residues 53 to 60, HV4 comprises residues 61 to 65, FW3b comprises residues 66 to 85, CDR3 comprises residues 86 to 105 and FW4 comprises residues 106 to 113, or any combination thereof, in which one or more residues may be absent from CDR3, suitably 1 to 12 residues, with respect to the consensus sequence.

In certain preferred embodiments of the invention, the single domain specific binding molecule has an amino acid sequence selected from the group consisting of VNAR domains shown in FIG. 2(a) or FIG. 2(b), or any combination thereof.

In one embodiment of the invention, the single domain specific binding molecule is an amino acid sequence as shown in FIG. 2(a) or 2(b) or any variant, analogue, derivative or fragment thereof, including a sequence having 50% identity thereto. Such sequences may be selected from the group consisting of: huE06 v1.1, huH08 v1.1, huE06 v1.2, huE06 v1.3, huE06 v1.4, huE06 v1.5, huE06 v1.6, huE06 v1.7, huE06 v1.8, huE06 v1.9, or huE06 v1.10, as shown in FIG. 2 or any combination thereof, or a sequence having 50% identity thereto. The single domain specific binding molecule known as E06 is suitably an isolated protein or peptide sequence comprising the nucleotide and amino acid sequences shown in FIG. 1(b).

In other embodiments of the invention, the specific binding molecule may be huE06 v1.10 as shown in FIG. 2(c) or any variant, analogue, derivative or fragment thereof, including a sequence having 50% identity thereto.

In one embodiment of the invention, the single domain specific binding molecule is humanized. The degree of humanization may be designed according to the antibody properties required, including antibody affinity. A suitable degree of humanisation may be 50%, or 55%, 60%, 65%, 70%, 75%, 80%, 85%, 90% or 95% homology to the corresponding human germline sequence for a Framework Region or a CDR Region specific to the antigen epitope of interest. For example, sequence huE06 v1.10 is approximately 60% humanized with respect to the native E06 sequence.

The single domain specific binding molecule may comprise additional N-terminal or C-terminal sequences which are cleaved off prior to use which may assist in purification and/or isolation during processes for the production of the molecule as described herein. For example, $(Ala)_3(His)_6$ (SEQ ID NO: 90) at the C-terminal end of the molecule.

In one embodiment, the framework FW1 region may comprise an amino acid sequence of TRVDQSPSSLSASVGDRVTITCVLT (SEQ ID NO: 28), the framework FW2 region may comprise an amino acid sequence of TYWYQQKP (SEQ ID NO: 91), the hypervariable HV2 region may comprise an amino acid sequence of SNKEQISIS (SEQ ID NO: 26), the framework FW3a region may comprise an amino acid sequence of RYSESVN (SEQ ID NO: 92), the hypervariable HV4 region may comprise an amino acid sequence of KGTKS (SEQ ID NO: 27), the framework FW3b region may comprise an amino acid sequence of FTLTISSLQPEDFATYYC (SEQ ID NO: 93), and the framework FW4 region may comprise an amino acid sequence of GAGTKVEIK (SEQ ID NO: 32), or sequences having 50% identity thereto.

Single domain specific binding molecules of the invention may therefore be constructed of any of the amino acid sequences for the various regions disclosed herein according to the basic structure:

FW1-CDR1-FW2-HV2-FW3a-HV4-FW3b-CDR3-FW4

The domain described herein as E06 was isolated from an immunized shark library, has picomolar high affinity, and high selectivity for human albumin and improves the pharmacokinetics (PK) of a companion "dummy" protein (fused to both N- and C-termini) across three species (mouse, rat and monkey) giving a predicted half-life of 19 days in man.

Also included within the invention are variants, analogues, derivatives and fragments having the amino acid sequence of the protein in which several e.g. 5 to 10, or 1 to 5, or 1 to 3, 2, 1 or no amino acid residues are substituted, deleted or added in any combination. Especially preferred among these are silent substitutions, additions and deletions, which do not alter the properties and activities of the protein of the present invention. Also especially preferred in this regard are conservative substitutions where the properties of a fusion protein of the present invention are preserved in the variant form compared to the original form.

Variants therefore include fusion proteins comprising a single domain specific binding molecule according to the first aspect of the invention.

The fusion protein may comprise a single domain specific binding molecule of the present invention fused to a heterologous peptide or protein sequence providing a structural element to the fusion protein. In other embodiments, the fusion protein may comprise a single domain specific binding molecule of the present invention fused with a molecule having biological activity. The molecule may be a peptide or protein sequence, or another biologically active molecule. Such a conjugate may therefore comprise a non-protein biologically active molecule also.

For example, the single domain specific binding molecule may be fused to a heterologous peptide sequence which may be a poly-amino acid sequence, for example a plurality of histidine residues or a plurality of lysine residues (suitably 2, 3, 4, 5, or 6 residues), or an immunoglobulin domain (for example an Fc domain).

References to heterologous peptides sequences include sequences from other mammalian species, such as murine and human and any heterologous peptides sequences originated from other VNAR domains.

Where the fusion protein comprises a single domain specific binding molecule of the present invention fused with a molecule having biological activity, biologically active moiety may be a peptide or protein having biological activity such as an enzyme, immunoglobulin, cytokine or a fragment thereof. Alternatively, the biologically active molecule may be an antibiotic, an anti-cancer drug, an NSAID, a steroid, an analgesic, a toxin or other pharmaceutically active agent. Anti-cancer drugs may include cytotoxic or cytostatic drugs. Specific examples are described in greater detail below in relation to pharmaceutical compositions comprising such fusion proteins.

In some embodiments, the fusion protein may comprise a single domain specific molecule of the invention fused to another immunoglobulin variable or constant region, or another single domain specific molecule of the invention. In other words, fusions of the single domain specific binding molecules of the invention of variable length, e.g. dimers, trimers, tetramers, or higher multimer (i.e. pentamers, hexamers, heptamers octamers, nonamers, or decamers, or greater). In specific embodiments this can be represented as a multimer of monomer VNAR subunits.

In fusion proteins of the present invention, the single domain specific binding molecule may be directly fused or linked via a linker moiety to the other elements of the fusion protein. The linker may be a peptide, peptide nucleic acid, or polyamide linkage. Suitable peptide linkers may include a plurality of amino acid residues, for example, 4, 5, 6, 7, 8, 9, 10, 15, 20 or 25 amino acids, such as $(Gly)_4$ (SEQ ID NO: 94), $(Gly)_5$ (SEQ ID NO: 95), $(Gly)_4Ser$ (SEQ ID NO: 96), $(Gly)_4(Ser)(Gly)_4$ (SEQ ID NO: 97), or combinations thereof or a multimer thereof (for example a dimer, a trimer, or a tetramer, or greater). For example, a suitable linker may be $(GGGGS)_3$ (SEQ ID NO: 98). Alternative linkers include $(Ala)_3(His)_6$ (SEQ ID NO: 90) or multimers thereof. Also included is a sequence which has at least 50%, 60%, 70%, 80%, 90%, 95% or 99% identity, using the default parameters of the BLAST computer program provided by HGMP, thereto.

An example of a variant of the present invention is a fusion protein as defined above, apart from the substitution of one or more amino acids with one or more other amino acids. The skilled person is aware that various amino acids have similar properties. One or more such amino acids of a substance can often be substituted by one or more other such amino acids without interfering with or eliminating a desired activity of that substance. Such substitutions may be referred to as "non-conservative" amino acid substitutions.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced. Amino acid insertions relative to the sequence of the fusion protein above can also be made. This may be done to alter the properties of a substance of the present invention (e.g. to assist in identification, purification or expression, as explained above in relation to fusion proteins). Amino acid changes relative to the sequence for the fusion protein of the invention can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

A protein according to the invention may have additional N-terminal and/or C-terminal amino acid sequences. Such sequences can be provided for various reasons, for example, glycosylation.

The term "fusion protein" in this text means, in general terms, one or more proteins joined together by chemical means, including hydrogen bonds or salt bridges, or by peptide bonds through protein synthesis or both.

"Identity" as known in the art is the relationship between two or more polypeptide sequences or two or more polynucleotide sequences, as determined by comparing the sequences. In the art, identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic acids Research, 12, 387 (1984), BLASTP, BLASTN, and FASTA (Atschul et al., J. Molec. Biol. 215, 403 (1990).

Preferably, the amino acid sequence of the protein has at least 50% identity, using the default parameters of the BLAST computer program (Atschul et al., J. Mol. Biol. 215, 403-410 (1990) provided by HGMP (Human Genome Mapping Project), at the amino acid level, to the amino acid sequences disclosed herein.

More preferably, the protein sequence may have at least 55%, 60%, 65%, 66%, 67%, 68%, 69%, 70%, 75%, 80%, 85%, 90% and still more preferably 95% (still more preferably at least 96%, 97%, 98% or 99%) identity, at the nucleic acid or amino acid level, to the amino acid sequences as shown herein.

The protein may also comprise a sequence which has at least 50%, 55%, 60%, 65%, 66%, 67%, 68%, 69%, 70%, 75%, 80%, 85%, 90%, 95%, 96%, 97%, 98%, or 99% identity with a sequence disclosed herein, using the default parameters of the BLAST computer program provided by HGMP, thereto.

According to a second aspect of the invention, there is provided a nucleic acid encoding a single domain specific binding molecule of the second aspect of the invention.

According to a third aspect of the invention, there is provided a nucleic acid construct comprising a nucleic acid of the second aspect of the invention.

The term "nucleic acid construct" generally refers to any length of nucleic acid which may be DNA, cDNA or RNA such as mRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

The nucleic acid construct of the third aspect of the invention may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard.

The nucleic acid construct of the third aspect of the invention preferably includes a promoter or other regulatory sequence which controls expression of the nucleic acid. Promoters and other regulatory sequences which control expression of a nucleic acid have been identified and are known in the art. The person skilled in the art will note that it may not be necessary to utilise the whole promoter or other regulatory sequence. Only the minimum essential regulatory element may be required and, in fact, such elements can be used to construct chimeric sequences or other promoters. The essential requirement is, of course, to retain the tissue and/or temporal specificity. The promoter may be any suitable known promoter, for example, the human cytomegalovirus (CMV) promoter, the CMV immediate early promoter, the HSV thymidinekinase, the early and late SV40 promoters or the promoters of retroviral LTRs, such as those of the Rous Sarcoma virus (RSV) and metallothionine promoters such as the mouse metallothionine-I promoter. The promoter may comprise the minimum comprised for promoter activity (such as a TATA elements without enhancer elements) for example, the minimum sequence of the CMV promoter. Preferably, the promoter is contiguous to the nucleic acid sequence.

As stated herein, the nucleic acid construct of the third aspect of the invention may be in the form of a vector. Vectors frequently include one or more expression markers which enable selection of cells transfected (or transformed) with them, and preferably, to enable a selection of cells containing vectors incorporating heterologous DNA. A suitable start and stop signal will generally be present.

The vector may be any suitable expression vector, such as pET. The vector may include such additional control sequences as desired, for example selectable markers (e.g. antibiotic resistance, fluorescence, etc.), transcriptional control sequences and promoters, including initiation and termination sequences. The promoter may be any suitable promoter for causing expression of the protein encoded by a nucleic acid sequence of the invention, e.g. a CMV promoter, human phosphoglycerate kinase (hPGK) promoter.

According to a fourth aspect of the invention, there is provided a host cell comprising a vector according to the third aspect of the invention. Representative examples of appropriate host cells for expression of the nucleic acid construct of the invention include virus packaging cells which allow encapsulation of the nucleic acid into a viral vector; bacterial cells, such as Streptococci, Staphylococci, *E. coli, Streptomyces* and *Bacillus subtilis*; single cells, such as yeast cells, for example, *Saccharomyces cerevisiae*, and *Aspergillus* cells; insect cells such as *Drosophila* S2 and *Spodoptera* Sf9 cells, animal cells such as CHO, COS, C127, 3T3, PHK.293, and Bowes Melanoma cells and other suitable human cells; and plant cells e.g. *Arabidopsis thaliana*. Suitably, the host cell is a eukaryotic cell, such as a CHO cell or a HEK293 cell.

Introduction of an expression vector into the host cell can be achieved by calcium phosphate transfection, DEAE-dextran mediated transfection, microinjection, cationic—lipid-mediated transfection, electroporation, transduction, scrape loading, ballistic introduction, infection or other methods. Such methods are described in many standard laboratory manuals, such as Sambrook et al, Molecular Cloning, a Laboratory Manual, Second Edition, Cold Spring Harbor Laboratory Press, Cold Spring Harbor, N.Y. (1989).

Mature proteins can be expressed in host cells, including mammalian cells such as CHO cells, yeast, bacteria, or other cells under the control of appropriate promoters. Cell-free translation systems can be employed to produce such proteins using RNAs derived from the nucleic acid construct of the third aspect of the present invention. Appropriate cloning and expression vectors for use with prokaryotic and eukaryotic hosts are described by Sambrook et al, Molecular Cloning, a Laboratory Manual, Second Edition, Cold Spring Harbor Laboratory Press, Cold Spring Harbor, N.Y. (1989).

According to a fifth aspect of the invention, there is provided a process for the production of a single domain specific binding molecule of the first aspect of the invention, comprising the step of expressing a nucleic acid sequence encoding said molecule in a suitable host cell as defined herein.

Proteins can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin and/or heparin chromatography. For therapy, the nucleic acid construct e.g. in the form of a recombinant vector, may be purified by techniques known in the art, such as by means of column chromatography as described in Sambrook et al, Molecular Cloning, a Laboratory Manual, Second Edition, Cold Spring Harbor Laboratory Press, Cold Spring Harbor, N.Y. (1989).

This aspect of the invention therefore extends to processes for preparing a fusion protein of the first aspect of the invention comprising production of the fusion protein recombinantly by expression in a host cell, purification of the expressed fusion protein and association of the pharmaceutically active agent to the purified fusion protein by means of peptide bond linkage, hydrogen or salt bond or chemical cross-linking. In some embodiments of this aspect of the invention where the pharmaceutically active agent is a peptide, the fusion protein could be prepared using hydrogen or salt bonds where the peptide is capable or multimerisation, for example dimerisation or trimerisation.

According to an sixth aspect of the invention, there is provided a pharmaceutical composition of a single domain specific binding molecule of the first aspect of the invention. Such compositions include fusion proteins comprising said single domain specific binding molecules.

The pharmaceutical composition may comprise a single domain specific binding molecule of the present invention fused to a therapeutic protein or a fragment thereof, or any other pharmaceutically active agent (non-protein based) or other chemical compound or polymer as described above. The conjugate may comprise therefore a biologically active agent fused to a single domain specific binding molecule of the invention.

The therapeutic protein may be a hormone, a growth factor (e.g. TGFβ, epidermal growth factor (EGF), platelet derived growth factor (PDGF), nerve growth factor (NGF), colony stimulating factor (CSF), hepatocyte growth factor, insulin-like growth factor, placenta growth factor); a differentiation factor; a blood clotting factor ( ); for example Factor VIIa, Factor VIII, Factor IX, VonWillebrand Factor or Protein C) or another protein from the blood coagulation cascade (for example antithrombin); a cytokine e.g. an interleukin, (e.g. IL1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 or IL-33 or an interferon (e.g. IFN-α, IFN-β and IFN-γ), tumour necrosis factor (TNF), IFN-γ inducing factor (IGIF), a bone morphogenetic protein (BMP, e.g. BMP-1, BMP-2, BMP-3, BMP-4, BMP-5, BMP-6, BMP-7, BMP-8, BMP-9, BMP10, BMP-11, BMP-12, BMP-13); an interleukin receptor antagonist (e.g. IL-1ra, IL-1RII); a chemokine (e.g. MIPs (Macrophage Inflammatory Proteins) e.g. MIP1α and MIP1β; MCPs (Monocyte Chemotactic Proteins) e.g. MCP1, 2 or 3; RANTES (regulated upon activation normal T-cell expressed and secreted)); a trophic factor; a cytokine inhibitor; a cytokine receptor; an enzyme, for example a free-radical scavenging enzyme e.g. superoxide dismutase or catalase or a pro-drug converting enzyme (e.g. angiotensin converting enzyme, deaminases, dehydrogenases, reductases, kinases and phosphatases); a peptide mimetic; a protease inhibitor; a tissue inhibitor of metalloproteinases (TIMPs e.g. TIMP1, TIMP2, TIMP3 or TIMP4) or a serpin (inhibitors of serine proteases).

In other embodiments of the invention, the therapeutic protein may be an antibody, or a engineered fragment thereof, including Fab, Fc, F(ab')$_2$ (including chemically linked F(ab')$_2$ chains), Fab', scFv (including multimer forms thereof, i.e. di-scFv, or tri-scFv), sdAb, or BiTE (bi-specific T-cell engager). Antibody fragments also include variable domains and fragments thereof, as well as other VNAR type fragments (IgNAR molecules).

The pharmaceutically active agent in such fusion proteins may be a therapeutic compound, e.g. anti-inflammatory drug (e.g. a non-steroidal anti-inflammatory drug), cytotoxic agent (e.g. a toxin, such as cholera toxin, or a radionuclide comprising a radioactive element for therapeutic or diagnostic use), cytostatic agent, or antibiotic. The other chemical compound or polymer may be a substance suitable to extend the half-life of the fusion protein in vivo. Suitable conjugates for use in such fusion proteins include polyethylene glycol (PEG) and/or cyclodextrin.

The pharmaceutical composition may be composed of a number of single domain specific binding molecules of the invention, for example dimers, trimers, or higher order multimers, i.e. 2, 3, 4, 5, 6, 7, or 8-mers, fused to the therapeutic protein.

The fusion of the single domain specific binding molecules of the invention to the therapeutic protein may at any convenient site on the protein and may be N-, C- and/or N-/C-terminal fusion(s). In one embodiment of the invention, the fusion of the single domain specific binding molecules of the invention is to both the N- and C-terminals of a therapeutic protein. Such fusion proteins may be prepared by any suitable route, including by recombinant techniques by expression in host cell or cell-free systems, as well as by chemical synthetic routes. Conjugates of non-protein biologically active agents or other chemical compounds or polymers may be achieved by any suitable chemical synthetic or biosynthetic (e.g. enzymatic) route.

Such compositions may comprise any suitable and pharmaceutically acceptable carrier, diluent, adjuvant or buffer solution. The composition may comprise a further pharmaceutically active agent. Such carriers may include, but are not limited to, saline, buffered saline, dextrose, liposomes, water, glycerol, ethanol and combinations thereof.

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

The pharmaceutical compositions may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg, 2 mg/kg or up to 4 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

According to a seventh aspect of the invention, there is provided a single domain specific binding molecule of the first aspect of the invention for use in medicine. This aspect of the invention therefore extends to the use of such of a single domain specific binding molecule of the first aspect in the manufacture of a medicament for the treatment of a disease in a patient in need thereof. A single domain specific binding protein of the invention can therefore be used to prepare a fusion protein comprising such a specific binding molecule as defined above in relation to pharmaceutical compositions of the invention.

Such uses also embrace methods of treatment of diseases in patients in need of treatment comprising administration to the patient of a therapeutically effective dosage of a pharmaceutical composition as defined herein comprising a single domain specific binding molecule of the first aspect of the invention.

As used herein, the term "treatment" includes any regime that can benefit a human or a non-human animal. The treatment of "non-human animals" in veterinary medicine extends to the treatment of domestic animals, including horses and companion animals (e.g. cats and dogs) and farm/agricultural animals including members of the ovine, caprine, porcine, bovine and equine families. The treatment may be a therapeutic treatment in respect of any existing condition or disorder, or may be prophylactic (preventive treatment). The treatment may be of an inherited or an acquired disease. The treatment may be of an acute or chronic condition. The treatment may be of a condition/disorder associated with inflammation and/or cancer. The single domain specific binding molecules of the invention may be used in the treatment of a disorder, including, but not limited to osteoarthritis, scleroderma, renal disease, rheumatoid arthritis, inflammatory bowel disease, multiple sclerosis, atherosclerosis, or any inflammatory disease.

The specific binding molecules of the present invention may also be used to investigate the nature of a disease condition in a patient. The single domain specific binding molecules may be used to prepare images of sites of disease in the body of a subject using imaging techniques such as X-ray, gamma-ray, or PET scanning, or similar. The invention may therefore extend to a method of imaging a site of disease in a subject, comprising administration of a suitably detectably labelled single domain specific binding molecule to a subject and scanning the subject's body subsequently. Alternatively, administration of said molecules to a subject may provide for a test result by analysing a sample from the subject following administration of the molecule. Such embodiments may include a method of diagnosis of a disease or medical condition in a subject comprising administration of a single domain specific binding molecule of the invention. The embodiment includes methods of detecting a site of disease or medical condition and specific binding molecules of the present invention for use in such methods.

Such uses of the specific binding molecules of the invention therefore extends to uses in research in cell culture in vitro where the specific binding molecule is used as a tool to investigate cellular processes and/or behaviour.

The present invention is based on an unexpected immune response based on IgNAR from a dogfish (*Squalus acanthias*) challenged with human serum albumin resulting in the isolation of a specific variable domain from a naturally evolved IgNAR. This invention shows for the first time that IgNAR forms part of the adaptive immune response of these animals that are approximately 200M years distinct in evolutionary terms from Nurse sharks who have previously been shown to respond to immunization (Dooley et al, Mol Immunol 40(1) 25-33 (2003). A high affinity, highly selective domain against HSA known as E06 was isolated after screening against target. Unusually for VNAR domain, the interface with target was planar as elucidated by the crystal structure. Unexpectedly E06 is tolerant of both N-terminal, C-terminal and dual partner protein fusions and has a predicted half-life (as a fusion) of 19 days in man as predicted by serum half-life analyses across three species. The isolation of this anti-HSA VNAR therefore has significant utility as a means for developing bi- or multi-valent therapeutically relevant constructs with extended sera half-life through fusion with the anti-HSA VNAR domain.

All preferred features of the second and subsequent aspects of the invention are as for the first aspect mutatis mutandis.

BRIEF DESCRIPTION OF THE DRAWINGS

FIGS. 1A to 1C show the amino acid sequences of the natural specific binding domains of the invention: a) an alignment of the anti-HSA binding domains isolated after round 2 and 3 of selection (SEQ ID NOs: 33-50); b) (i) the amino acid of the specific binding domain E06 (SEQ ID NO: 46); (ii) a comparison of sequence E06 (SEQ ID NO: 46) and BB11 (SEQ ID NO: 85); and (iii) sequence E06 with a 3×Ala-6×HIS tag (AAA-6×His tag is in italic) (SEQ ID NO: 51); c) sequence alignment of anti-HSA binding domains isolated from the pre-selected phage display library (SEQ ID NOs: 52-64). (Shading (with solid grey) indicates residues that differ from the consensus in FIG. 1(*a*) and 1(*c*)).

FIGS. 2A to 2C: (a) shows structural sequence alignment of VNAR E06 (SEQ ID NO: 46) and its humanized variants of the invention (SEQ ID NOs: 65-74) including human germline V-kappa light chain DPK9/JK1 (SEQ ID NO: 65), shark VNAR 5A7 (SEQ ID NO: 66), and a humanized 5A7 variant, 5A7-IVabc (SEQ ID NO: 67). The residue numbering refers to E06 sequence; (b) individual amino acid sequences of the humanized VNAR domains of the invention: 5A7 (5A7 IVabc) (SEQ ID NO: 67), humanized versions of the anti-HSA domain E06 versions 1.1 through to 1.10 and H08 version 1.1 (SEQ ID NOs: 68-78); (c) alignment of (SEQ ID NO: 46), humanized E06v1.10 (SEQ ID NO: 74), and improved versions of the humanized E06 v1.10 of the invention (SEQ ID NOs: 79-89).

68) and v1.10 (SEQ ID NO: 74) are also aligned so illustrate the re-introduction of contact residues in v1.10 post crystal dataset.

FIGS. 4A to 4E show ability of E06 to extend the serum half-life of an unrelated domain across three species of PK model; (a) in vivo PK analyses of E06 and H08 in fusion with 2V as measured via iodination, 2V alone and PEGylated 2V as a PK control; (b) (i) LC-MS measurements of half-life of 2V-E06 and (ii) 2V-E06-2V in a murine model of PK both intra-venous and subcutaneous administration; (c) E06-2V and 2V-E06 in a rat model of PK by intra-venous administration; (d) E06-2V and 2V-E06 both intra-venous and subcutaneous administrations in a cynomologus monkey model of PK with E06-2V also as subcutaneous administration; (e) allometric scaling of 2V-E06 based on data attained and compared to half-life of albumin in each species.

FIGS. 5A and 5B show the retention of the therapeutic domains A1 and CC3 to still bind target and retain functionality when in fusion to E06; (a) cell neutralization assays showing the ability of anti-mICOSL domains A1 and CC3 to still prevent ligand-receptor binding; (b) T-cell proliferation assays showing the ability of A1 and CC3 to retain the ability to inhibit T-cell proliferation when in complex with E06 (i) (hFc controls shown in (ii).

The invention will also be further described by way of reference to the following Examples which are present for the purposes of illustration only and are not to be construed as being limiting on the invention.

The abbreviations used are:

HSA, BSA, MSA, RSA—human, bovine, mouse and rat serum albumin, respectively; HBS, HEPES-buffered saline; HEL, hen egg lysozyme; CDR, complementarity determining region; CM, conditioned medium; FW, framework region; HV, hypervariable region; HRP, horseradish peroxidase; MME, monomethyl ether; PBS, phosphate-buffered saline; PEG, polyethylene glycol; RMSD, root mean squared deviation; LC-MS, liquid chromatography mass spectrometry.

EXAMPLE 1

Isolation of human serum albumin-binding shark VNARs

As a prerequisite to this work, a sequence database of approximately 1600 VNAR sequences from the Spiny dogfish (*Squalus acanthias*) were compiled, aligned and analysed to facilitate the design of primer pairs to capture the immune repertoire. This ensured the subsequent immune phage libraries constructed were as representative as possible and lacked bias toward certain isotypes. Spiny dogfish were immunized with human serum albumin and VNAR sequences from a seropositive animal were isolated and made into a phage display library. The library was rescued and a solid phase sequential bio-panning strategy against 50 □g/ml, 50 g/ml and 0.5 □g/ml HSA was employed. After three rounds several high affinity, highly similar clones against albumin were isolated (FIG. 1(*a*)). Binding at both pH 7.0 and pH 6.0 (to facilitate lyzosomal recycling) was incorporated as part of the screening strategy. One of the best binders, which reacted to HSA, MSA and RSA at pH 7.0 and pH 6.0, was called E06 (FIG. 1(*b*)).

VNAR clone E06 is 103 residues in length and has low sequence similarity to human variable domain sequences (<30% identity), with the closest human germline sequences being from VL6 and VH4 families. E06 sequence is a typical shark VNAR lacking the CDR2 region of mammalian antibody V domains and carrying instead a HV2 stretch in FW2 and also HV4 loop as part of FW3 sequence. Similar to other Ig molecules, there is a 6-amino acid CDR1 sequence and relatively short 9-amino acid CDR3 sequence (FIG. 1(*b*)). E06 belongs to a structural type IV of shark VNARs, which is distinct from better-characterized type I (e.g. 5A7 (Dooley et al, Mol Immunol 40(1) 25-33 (2003)) and type II (e.g. PBLA8; a phage-display library clone from HEL-immunized nurse shark) (Dooley et al, PNAS 103(6) 1846-51 (2006))). Type IV VNARs have only 2 canonical Ig domain cysteine residues (positions 22 and 83 in E06), compared to 6 cysteines in type I and 4 cysteines in type II.

The immunized library was also screened prior to panning which resulted in the isolation of several more diverse anti-HSA VNAR domains (FIG. 1(*c*)). The response was sufficiently robust that selection was not necessary as the unselected library showed 16% positive binding to HSA.

EXAMPLE 2

Humanization Strategy for Type I and Type IV VNARs

As an initial strategy the well characterized type I VNAR, 5A7 was humanized. To this end, we selected as a template the human Ig variable light domain (V01) germline sequence, DPK9, which was considered structurally the closest to 5A7 of human Ig variable domain sequences. 5A7 was humanized by resurfacing, whereby multiple solvent-exposed as well as core framework residues of 5A7 were replaced by human DPK9/J01 residues (FIG. 2(*a*)). Specifically, the following structural elements were replaced in 5A7: FW1 (residues 6-21), FW2/part of HV2 (residues 38-47), FW3b (residues 67-82) and FW4 (residues 106-113). All six cysteine residues of type I VNAR scaffold were retained. The resulting molecule, which we call 5A7-IVabc, has 60 out of 86 (69.8%) of non-CDR residues, and 60 out of 112 (53.6%) of all residues identical to DPK9

To further validate the humanization-by-resurfacing approach taken with 5A7, we created a series of humanized variants of E06 using 5A7-IVabc molecule as a guide as well as using the crystal structure to ensure critical interface residues remained within the humanized variants to retain function of the original domain (FIG. 2(*a*)). To make humanized E06 variant 1.1 (huE06 v1.1), 30 residues out of 103 total in E06 were replaced with DPK9 residues. Specifically, the majority of framework residues: FW1 (residues 6-21), FW2 (residues 38-40), FW3b (residues 66-82), and FW4 (residues 99-103) of E06 were made identical to DPK9. The majority of these changes parallel those used to make 5A7-IVabc. The regions left intact (shark) were first 4 amino-terminal residues, CDR1 (residues 28-33) and CDR3 (residues 86-94), HV2 (residues 43-52), FW3a and HV4 (residues 53-65). In huE06 v1.1 molecule, 54 out of 85 (63.5%) of non-CDR residues are identical to human DPK9.

To modify E06 further, mutations toward 5A7-IVabc sequence were introduced into HV4 region of v1.1 (K61S and T63S) to make huE06 v1.2. Further DPK9-like changes were made in HV2 region ($^{43}$SSNKE$^{47}$→$^{43}$KAPK$^{46}$) (SEQ ID NOs: 99 & 100) to produce huE06 v1.7. These two sets of changes (in HV2 and HV4) were combined to make huE06 v1.3. A derivative of v1.3, which had its N-terminus changed toward DPK9 ($^{1}$TRVD$^{4}$ to $^{1}$DIQMT$^{5}$) (SEQ ID NOs: 101 & 102), was made and named huE06 v1.4. We also attempted to redesign E06 by shortening the FW3a/HV4 region; to do that, 5 shark residues were deleted and 3 DPK9 residues introduces in this area of huE06 v1.3 molecule; in addition, Y55F change was introduced. The resulting molecule was named huE06 v1.5. Finally, huE06 v1.10 was derived from v1.1 by restoring $^{38}$RKN$^{40}$ shark sequence in FW2 from DPK9-like $^{38}$QQK$^{40}$.

During this step wise process, a total of 10 humanized derivatives of E06 were designed, expressed and characterized—these sequences are listed in FIG. 2(b). Additional variants of v1.10 with improved biophysical characteristics were constructed using random mutagenesis, a phage display library built from these variants and screened on the basis of retention to bind HSA. Briefly, hE06v1.10 sequence was cloned into a phagemid vector and was mutated by error-prone PCR aiming at up to 9 substitutions/VNAR sequence using a GeneMorph II random mutagenesis kit (Agilent Technologies, Santa Clara, Calif.) according to the manufacturer's instructions. The resultant mutational phage display libraries were rescued and selected twice using Nunc Maxisorp immunotubes. Following each pan, two 96-well plates of individual colonies were picked with a QPix2 XT (Genetix, San Jose, Calif., USA). Binding as monoclonal phage and periprep was evaluated by ELISA. All samples were processed with a Perkin Elmer MiniTrak robotic liquid handling system (Waltham, Mass., USA). Unique clones showing OD450 by periprep ELISA at least 25% higher than the readings obtained from parental hE06v1.10 were selected for transfer to a eukaryotic expression vector. Following preliminary screen, clones exhibiting the best binding properties were selected for expression transiently in 1 litre cultures of HEK293 cells and monomeric 6×His tagged VNAR proteins purified by IMAC and cation IEX chromatography. The clones with the best biophysical propertied based on HSA binding and no evidence of aggregation are listed in FIG. 2(c).

EXAMPLE 3

Structure of E06 in Complex with HSA

Figure 3A:
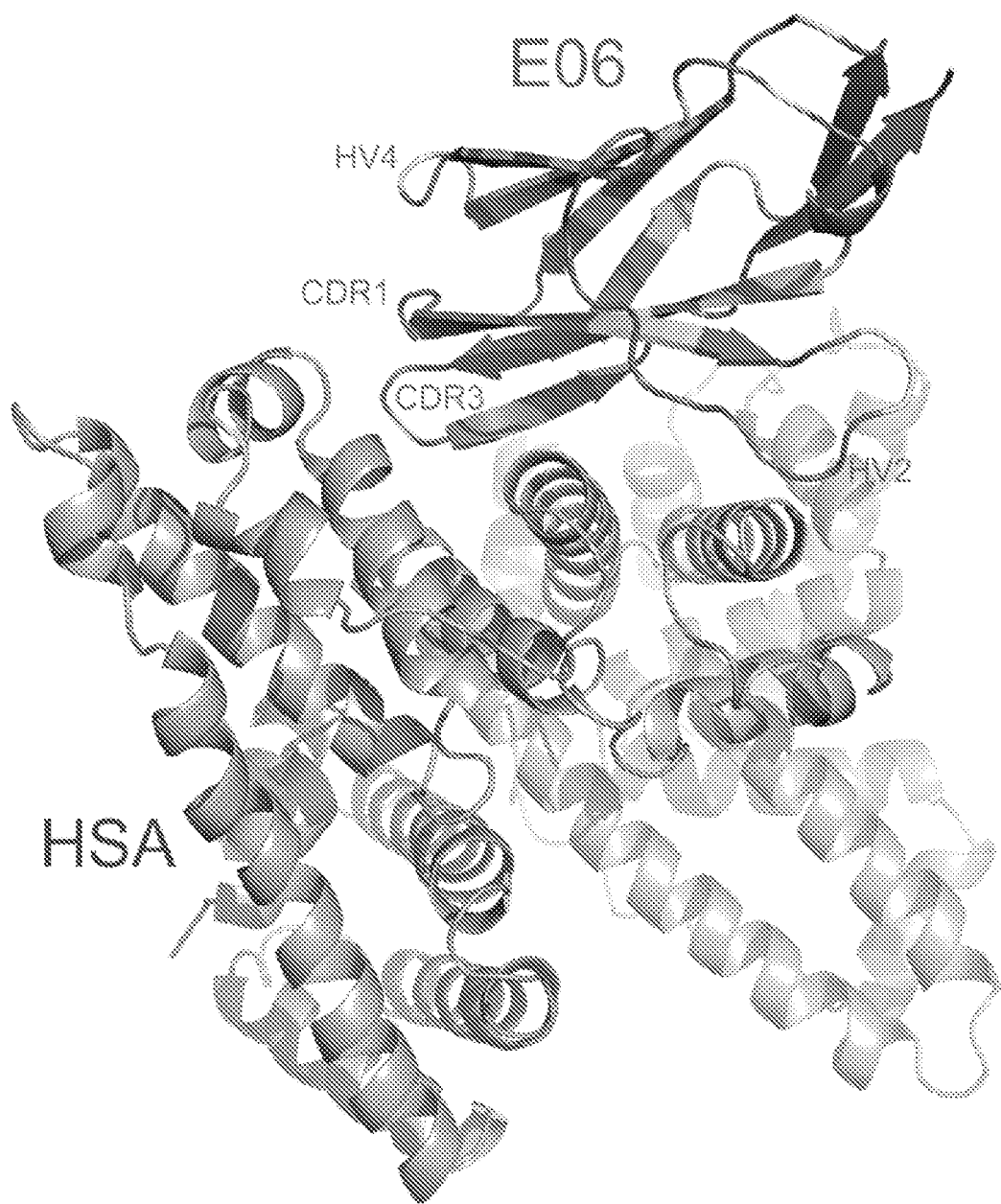
FIGS. 3A and 3B show: (a) a ribbon model representation of the crystal structure of E06 in complex with HSA; (b) sequence of E06 (SEQ ID NO: 46) highlighting-, CDR1, CDR3, HV2 and HV4 and framework regions. Residues identical to human V kappa framework DPK9 are shown in bold. Residues within 5A of HSA in crystal structures, and involved in various modes of interactions with HSA, are marked by arrows. Humanized sequences v1.1 (SEQ ID NO.

E06 was expressed as a monomeric 6×His-tagged protein and crystallized in complex with HSA and the structure was determined to 3.0 Å (FIG. 3(a)).

Protocols: Crystallization

E06:HSA crystals were grown by hanging drop vapor diffusion at 18° C. in drops containing 1.0 μl protein stock solution (11.0 mg/ml protein complex, 25 mM Tris pH 7.4, 150 mM NaCl) mixed with 1.0 μl well solution (16% PEG 2000 MME, 100 mM sodium acetate pH 4.6) and equilibrated against 0.5 ml of well solution. Chunky crystals grew in approximately one week, measuring ~50 μm across.

Data Collection and Processing

E06 complex crystals belong to the space group P3221 with unit cell parameters 127.98×127.98×151.76 Å, and contain two molecules of E06 and two molecules of HSA in the asymmetric unit, implying a solvent content of 54.2%. Crystals were drawn through a solution of 20% DMSO and 80% well solution, and cooled rapidly in liquid nitrogen.

Diffraction data were recorded at APS beamline 22-ID on a MAR-300 detector. Intensities were integrated and scaled using the program Xia2.

Phasing, Model Building, and Refinement

Figure 3B:
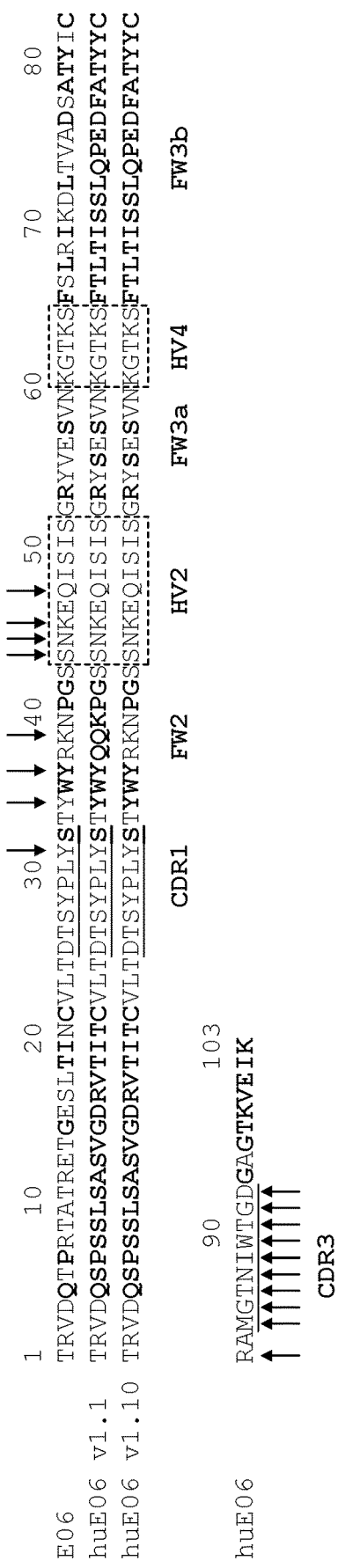

The structure of E06 in complex with HSA was determined by molecular replacement with PHASER using the crystal structure of apo HSA (PDB ID: 1AO6) as a starting search model. A few rounds of refinement with Phenix were performed, after which clear density for the p-sheet regions of EO6 was obtained. After subsequent placement of a poly-alanine model of EO6 and several iterative cycles of model rebuilding with Coot and refinement with autoBuster, the final Rwork and Rfree values of 23.73% and 26.63% were obtained. In contrast to the classical antigen-antibody recognition mode, it was found that most extensive interactions with HSA originate from the CDR3 residues and framework residues on E06 (FIG. 3(b)). Antigen binding results in a large buried surface area of 705 Å, which is 12.5% of total surface area of E06. The interaction elucidated is also unusual for a VNAR due to the planar nature of the interface and inclusion and contribution of framework residues in the antigen-antibody complex.

EXAMPLE 4

Functional properties of humanized E06 variants

5A7-IVabc protein showed excellent expression profile in mammalian cells with very little aggregation in either monomeric or dimeric (with human Fc) format and full retention of binding activity to HEL. The binding constant for monomeric VNARs to HEL, as determined by Biacore, was 13.6 nM for parental 5A7 and 14.8 nM for humanized 5A7-IVabc (Table 1). The results show the retention of binding antigen by humanized VNAR domains of the invention as measured by BIAcore against target; (Table 1) shows retention of binding of humanised 5A7 to hen egg lysozyme (HEL); (Table 2 and 3) shows retention of albumin binding by humanized E06 v1.1 and v1.10 to human, mouse and rat albumin at pH 7.4 and pH 6.0.

TABLE 1

| Sample | ka (1/Ms) | kd (1/s) | KD (M) | KD (nM) | Rmax (RU) | tc | Chi$^2$ (RU$^2$) | % surface active |
|---|---|---|---|---|---|---|---|---|
| 5A7-AAA-6xHis | 4.48E+06 | 6.09E−02 | 1.36E−08 | 13.6 | 61.76 | 5.47E+07 | 0.31 | 65.0% |
| 5A7IVabc-AAA-6xHis | 1.17E+07 | 1.73E−01 | 1.48E−08 | 14.8 | 69.67 | 6.26E+07 | 0.272 | 74.1% |

E06 and its humanized variants were first expressed as human Fc fusions. The expression levels of the humanized variants, such as 1.1, 1.2, 1.3, 1.5 and 1.7, were not dramatically different from the parental E06 molecule and were in 10-40 μg/ml range in transient COS-1 system.

To assess the kinetic parameters of binding of E06, huE06 v1.1 and huE06 v1.10 to serum albumins, the monomeric (6×His-tagged) V-NARs were tested in BIAcore experiments. As shown in Table 2 (at pH 7.4) and Table 3 (at pH 6.0), the humanized versions retained the ability to bind mammalian albumin species with nanomolar affinities. Increased affinity of the humanized versions was seen at the lower pH values compared of wild type E06.

TABLE 2

| IgNAR | Albumin | ka (1/Ms) | kd (1/s) | KD (nM) | Fold change from E06 | Rmax (RU) | % Surface Active | Chi$^2$ (RU$^2$) |
|---|---|---|---|---|---|---|---|---|
| E06 | human | 3.48E+06 | 6.55E−04 | 0.19 | n/a | 86.18 | 85.3% | 0.81 |
| huE06v1.1 | human | 8.72E+05 | 1.40E−02 | 16.0 | 84.9 | 78.6 | 77.8% | 0.234 |
| huE06v1.10 | human | 5.59E+05 | 3.57E−03 | 6.4 | 33.9 | 80.62 | 79.8% | 0.181 |
| E06 | mouse | 2.18E+06 | 1.80E−03 | 0.83 | n/a | 109.9 | 85.2% | 0.871 |
| huE06v1.1 | mouse | 8.41E+05 | 4.14E−02 | 49.2 | 59.4 | 100.9 | 78.2% | 0.354 |
| huE06v1.10 | mouse | 4.12E+05 | 9.59E−03 | 23.2 | 28.1 | 100.9 | 78.2% | 0.26 |
| E06 | rat | 2.21E+06 | 3.20E−03 | 1.45 | n/a | 93.71 | 88.4% | 0.687 |
| huE06v1.1 | rat | 4.36E+05 | 3.29E−02 | 75.3 | 52.0 | 77.32 | 72.9% | 0.616 |
| huE06v1.10 | rat | 4.49E+05 | 1.65E−02 | 36.8 | 25.4 | 84.03 | 79.3% | 0.311 |

TABLE 3

| IgNAR | Albumin | ka (1/Ms) | kd (1/s) | KD (nM) | Fold change from E06 | Rmax (RU) | % Surface Active | Chi$^2$ (RU$^2$) |
|---|---|---|---|---|---|---|---|---|
| E06 | human | 1.12E+07 | 1.59E−03 | 0.14 | n/a | 50.1 | 49.6% | 0.254 |
| huE06 v1.1 | human | 3.62E+06 | 1.84E−02 | 5.07 | 35.6 | 29.3 | 29.0% | 0.196 |
| huE06 v1.10 | human | 3.52E+06 | 6.37E−03 | 1.81 | 12.7 | 39.7 | 39.3% | 0.334 |
| E06 | mouse | 9.85E+06 | 3.23E−03 | 0.33 | n/a | 44.1 | 34.2% | 0.259 |
| huE06 v1.1 | mouse | 3.43E+06 | 3.18E−02 | 9.28 | 28.3 | 21.0 | 16.3% | 0.143 |
| huE06 v1.10 | mouse | 3.14E+06 | 1.25E−02 | 3.98 | 12.2 | 31.7 | 24.5% | 0.182 |
| E06 | rat | 1.26E+07 | 4.33E−03 | 0.34 | n/a | 41.8 | 39.5% | 0.244 |
| huE06 v1.1 | rat | 3.12E+06 | 3.10E−02 | 9.94 | 29.0 | 18.5 | 17.4% | 0.118 |
| huE06 v1.10 | rat | 3.65E+06 | 1.52E−02 | 4.17 | 12.2 | 29.1 | 27.4% | 0.16 |

EXAMPLE 5

E06 Extends Plasma Half-Life of Unrelated Fusion Proteins In Vivo

The unrelated naïve VNAR domain, 2V, was identified as a type IV during the initial database acquisition of sequences. It has no known binding partner and was therefore chosen as a suitable "dummy" protein partner to study the PK and PD of E06 in several animal models. Molecular fusions of E06 with N-terminal, C-terminal and dual terminal constructs were created using G4S linker sequences bridging the VNAR domains, and C-terminal AAA-6×HIS tags for purification purposes. Dimers and trimers were expressed in HEK293 cells and purified using standard Ni-NTA methods and SEC as a final polishing step. Proteins were assessed for rodent viruses and endotoxin levels prior to use in animal models. BIAcore analysis was conducted to determine the affinities of each fusion variant compared to wild-type E06. Table 4 shows the on, off rates and KD affinity values for wild-type, 2V-E06, E06-2V and 2V-E06-2V fusions with 2V control and the anti-HEL 5A7 as an additional control. In particular Table 4 shows the BIAcore analyses of E06 alone, as an N-terminal, C-terminal and dual fusion construct with 2V, 2V alone and 5A7 as control binding to HAS.

TABLE 4

| Sample | Ligand | mean ka ± SE ($\times 10^6$ $M^{-1}$ $s^{-1}$) | mean kd ± SE ($\times 10^{-4}$ $s^{-1}$) | mean KD ± SE (nM) | n |
|---|---|---|---|---|---|
| E06 | HSA | 3.092 ± 0.034 | 5.825 ± 0.103 | 0.189 ± 0.005 | 4 |
| | CSA | 2.675 ± 0.023 | 5.845 ± 0.185 | 0.219 ± 0.005 | 2 |
| | MSA | 2.316 ± 0.010 | 17.130 ± 0.360 | 0.740 ± 0.012 | 2 |
| | RSA | 2.240 ± 0.058 | 30.110 ± 0.110 | 1.345 ± 0.030 | 2 |
| | HEL | — | — | — | 2 |
| E06-2V | HSA | 7.464 ± 0.384 | 5.307 ± 0.147 | 0.071 ± 0.002 | 4 |
| | CSA | 8.996 ± 0.841 | 5.915 ± 0.370 | 0.066 ± 0.002 | 2 |
| | MSA | 5.299 ± 0.463 | 14.695 ± 0.415 | 0.279 ± 0.017 | 2 |
| | RSA | 5.553 ± 0.452 | 27.510 ± 0.310 | 0.498 ± 0.035 | 2 |
| | HEL | — | — | — | 2 |
| 2V-E06 | HSA | 0.953 ± 0.097 | 6.412 ± 0.116 | 0.721 ± 0.095 | 6 |
| | CSA | 0.820 ± 0.138 | 6.821 ± 0.163 | 0.910 ± 0.157 | 4 |
| | MSA | 0.862 ± 0.018 | 21.420 ± 0.150 | 2.486 ± 0.036 | 2 |
| | RSA | 0.623 ± 0.091 | 34.418 ± 0.550 | 5.949 ± 0.984 | 4 |
| | HEL | — | — | — | 2 |
| 2V-E06-2V | HSA | 0.689 ± 0.064 | 5.762 ± 0.068 | 0.896 ± 0.091 | 8 |
| | CSA | 0.592 ± 0.069 | 5.904 ± 0.186 | 1.052 ± 0.155 | 4 |
| | MSA | 0.507 ± 0.047 | 19.783 ± 0.473 | 4.032 ± 0.472 | 4 |
| | RSA | 0.448 ± 0.041 | 31.353 ± 0.919 | 7.245 ± 0.934 | 4 |
| | HEL | — | — | — | 4 |
| 2V | HSA | — | — | — | 4 |
| | CSA | — | — | — | 2 |
| | MSA | — | — | — | 2 |

TABLE 4-continued

| Sample | Ligand | mean ka ± SE ($\times 10^6$ M$^{-1}$ s$^{-1}$) | mean kd ± SE ($\times 10^{-4}$ s$^{-1}$) | mean KD ± SE (nM) | n |
|---|---|---|---|---|---|
| | RSA | — | — | — | 2 |
| | HEL | — | — | — | 2 |
| 5A7 | HSA | — | — | — | 2 |
| | CSA | N.A. | N.A. | N.A. | — |
| | MSA | — | — | — | 2 |
| | RSA | N.A. | N.A. | N.A. | — |
| | HEL | 1.543 ± 0.025 | 468.450 ± 11.350 | 30.365 ± 0.255 | 2 |

The data shows that E06 tolerates bath N-terminal and C-terminal fusions creating dimers proteins in addition to both N and C terminal fusion constructs creating trimers. All constructs retain high affinity binding to target (HSA) and across other albumin species (mouse, rat and monkey). Note that in Table 4, "-" indicates no binding and N.A. that the experiment was not conducted. All three constructs were tested in animal model of PK to measure the ability of E06 to extend plasma half-life of an unrelated partner protein. As an initial study, EOG (SEQ ID NO: 46) and the related protein H08 (sequence listed in FIG. 1(a) as P2_H08, SEQ ID NO: 36, was isolated from same panning strategy as E06) were fused to 2V and compared to the clearance of 2V alone. Purified E06-2V and H08-2V were studied in a murine single dose, PK model to determine the serum half-life of 2V as an independent domain or in complex with the anti-HSA VNAR domains. To ensure iodination did not affect HSA binding, E06-2V and H08-2V were "cold" iodinated showing that this did not interfere with E06 binding HSA.

Figure 4A:
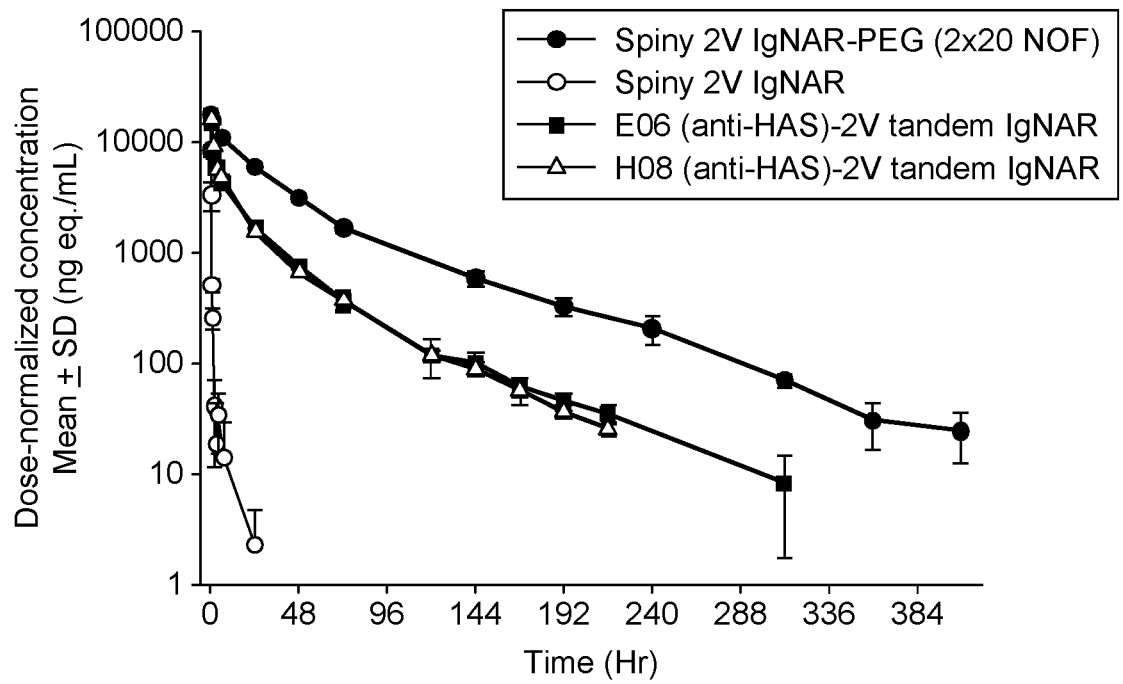
Figure 4B:
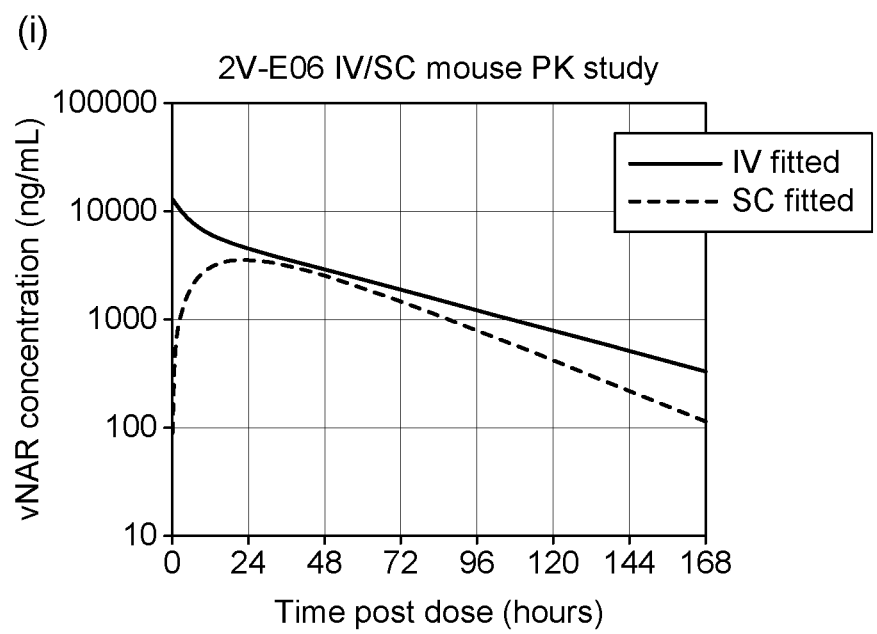
Figure 4B:
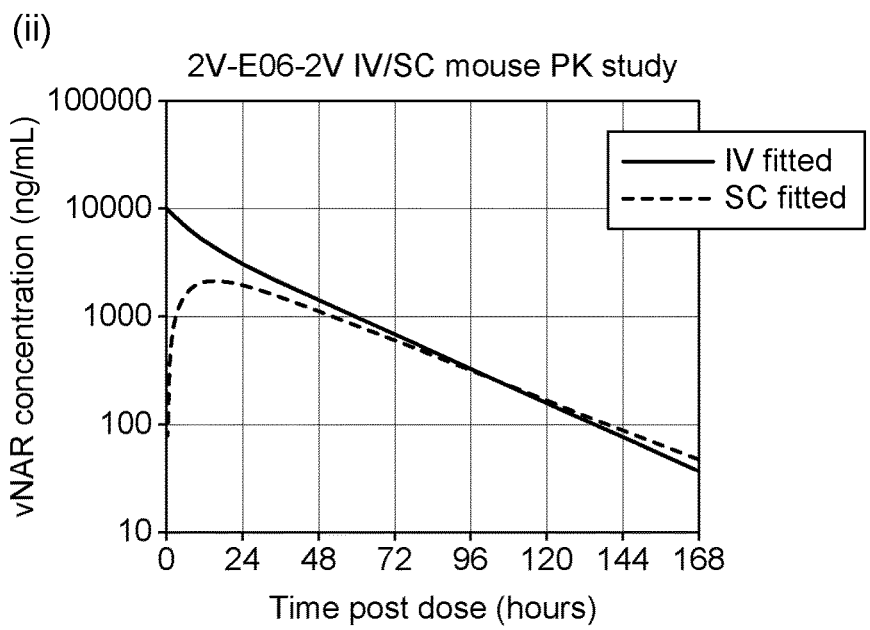
Figure 4C:
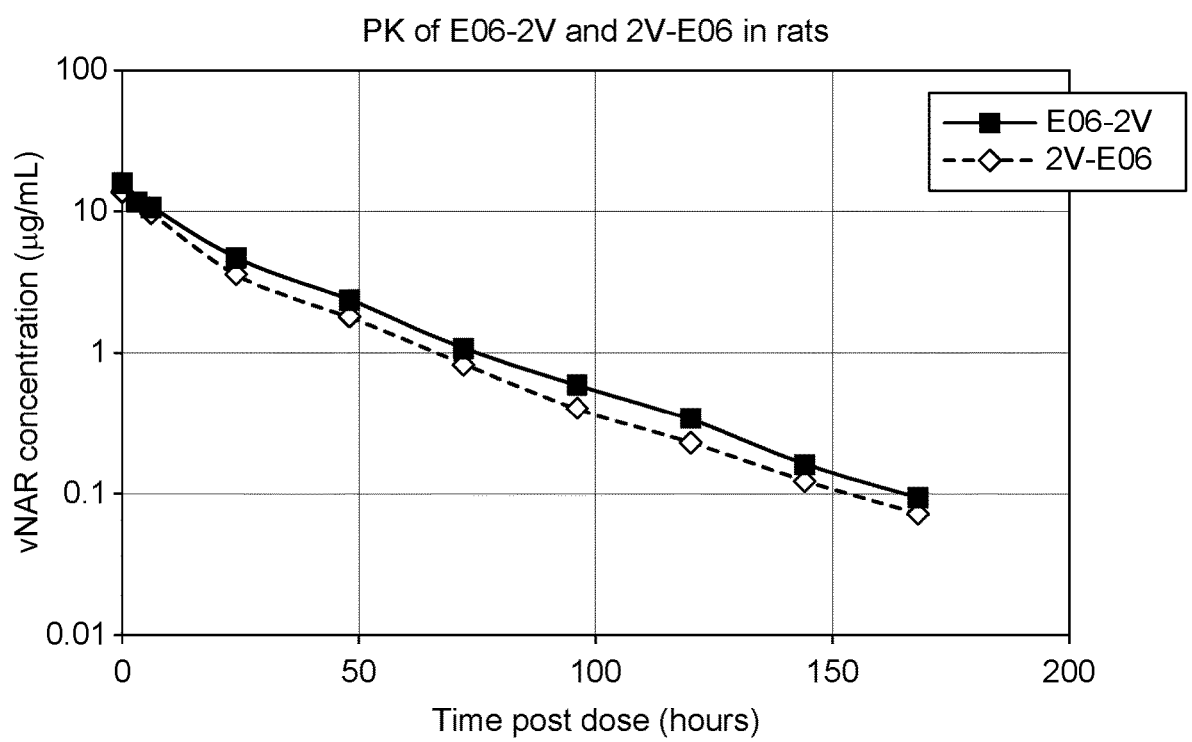
Figure 4D:
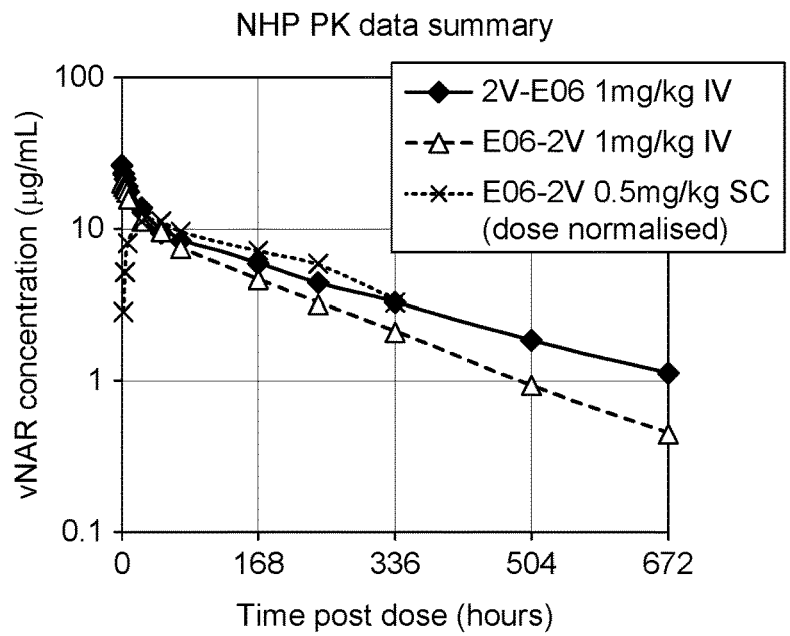
Figure 4E:
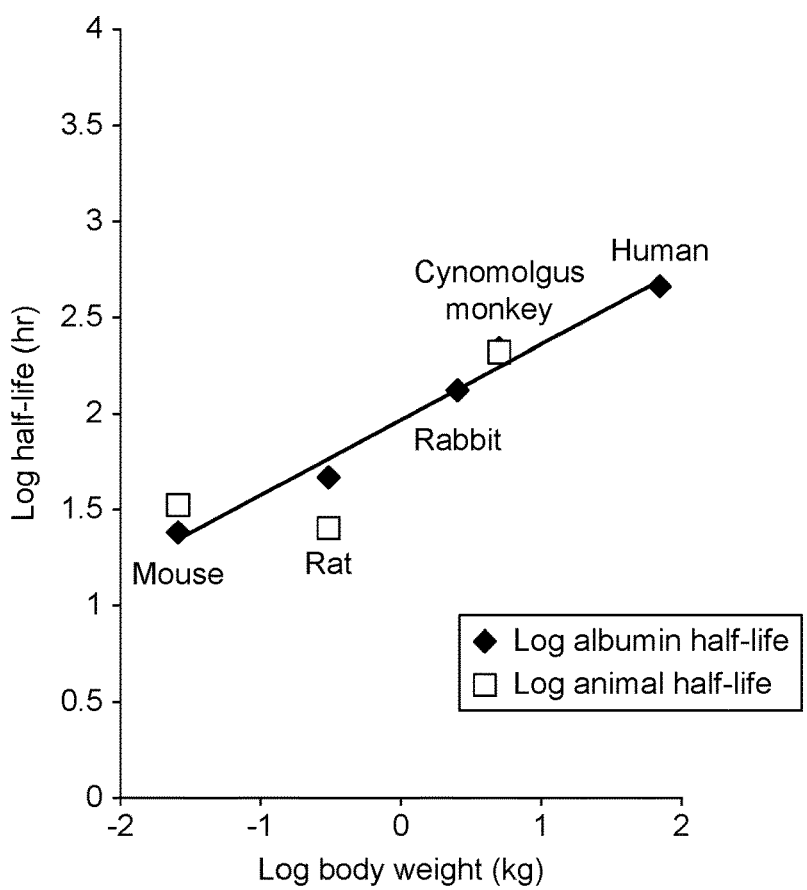

Male C57BL/6 mice were injected i.v. with the following doses of protein: 1 mg/kg for 2V and 2V-PEG (2×NOF) and 0.3 mg/kg for the tandem VNARs (E06-2V and H08-2V). The concentrations for tandem VNARs were scaled for 1 mg/kg dosage and the dose for 2V-PEG was based on protein only. Radioactive equivalent concentrations were determined by gamma-counting. Individual concentration values <LOQ (defined as 3*background cpm) were treated as zero for calculations of the mean and SD; N=6 per time point. Plasma concentration are illustrated in FIG. 4(a) and PK parameters summarized in Table 5 which shows PK and PD measurements showing increase in half-life of E06 fusion with 2V compared to 2V alone.

Figure 5A:
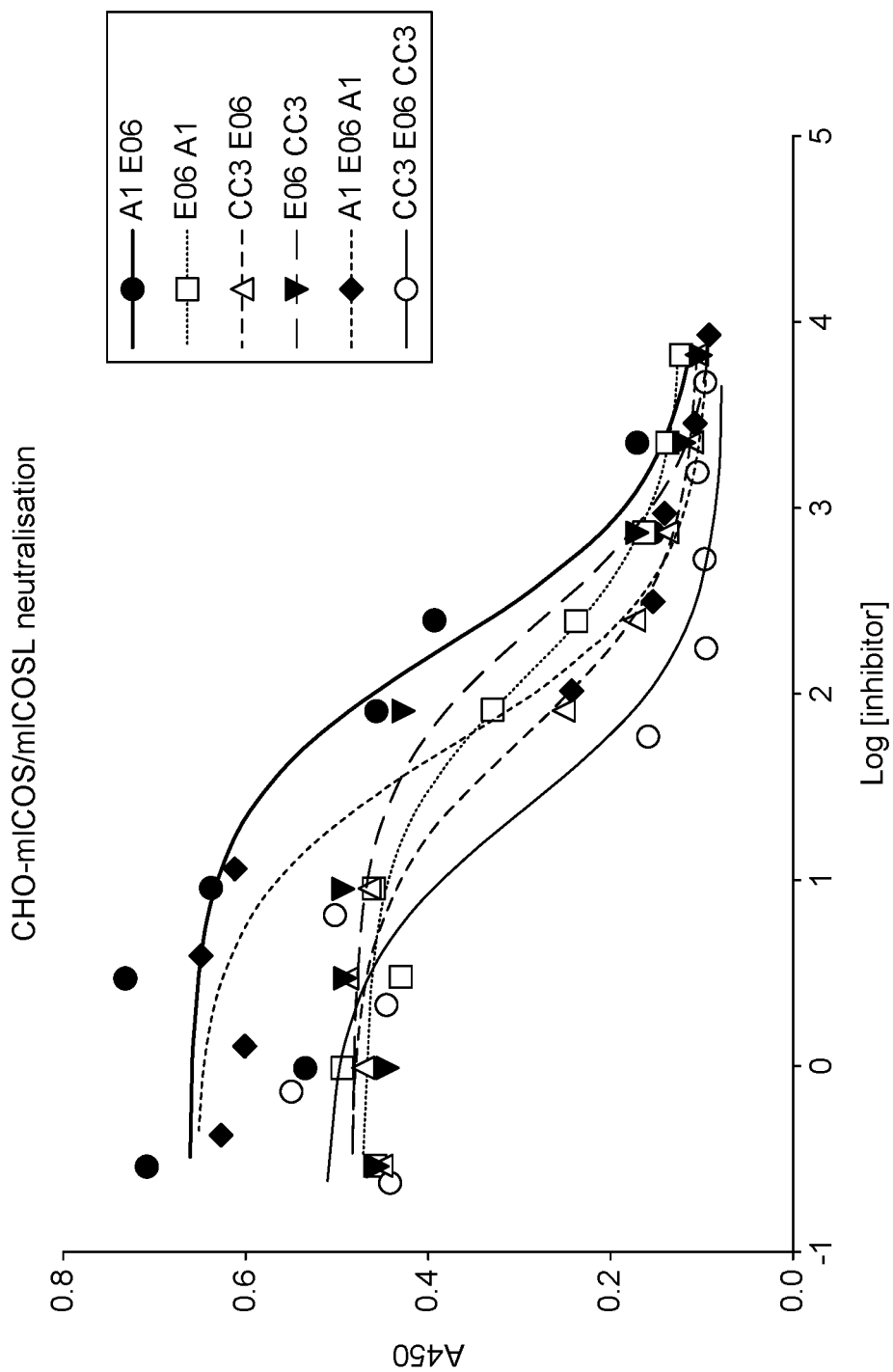

The resultant measured half-life is shown in FIG. 5(b) clearly showing that E06 and H08 extended the plasma half-life of 2V from approximately 9 minutes to 47.8 h and 39.7 h respectively.

As a more precise means of measuring protein clearance and ensuring that fusion partners are intact, an LC-MS method was carried out measuring peptides specific to E06 and 2V. For the mouse model, 2V-E06 and 2V-E06-2V were injected at a dose of 4 and 2 mg/kg, respectively, both i.v. and s.c. into groups of 12 CD1 mice. Two blood samples plus terminal bleeds were taken from each animal at intervals to provide duplicate samples to cover time points from 1 h-168 h (FIG. 5(b). For the rat model, E06-2V and 2V-E06 were injected i.v. at 1 mg/kg into groups of 3 wistar rats and blood samples taken from 0.25-168 h. A PK study in cynomolgus monkeys was carried out with E06-2V and 2V-E06 dosed at 1 mg/kg i.v. to groups of two animals. Blood sampling was carried out at from 0.25 h-28 days. After 28 days, the 2V-E06 group were injected s.c. with 0.5 mg/kg protein and sampling carried out over 14 days.

Table 6 summarizes the pharmacokinetic data measured from these experiments showing extended half-life of the E06 containing fusions, good correlation between intravenous and subcutaneous administration and rapid distribution where pharmacokinetic parameters were measured across all three PK models.

TABLE 6

| Species | Construct | Dose (mg/kg) | Route | Cl (ml/hr/kg) | Vdss (ml/kg) | t$^{1/2}$ (h) | F (%) |
|---|---|---|---|---|---|---|---|
| Rat | E06-2V | 1 | iv | 3.3 | 105 | 22 | — |
| | 2V-E06 | 1 | iv | 2.7 | 94 | 25 | — |
| Mouse | 2V-E06 | 4 | iv | 2 | 96 | 33 | — |
| | 2V-E06 | 4 | sc | — | — | 25 | 48 |
| | 2V-E06-2V | 2 | iv | 3.8 | 112 | 21 | — |
| | 2V-E06-2V | 2 | sc | — | — | 26 | 46 |

TABLE 5

| Compound (Protocol) | Dose (mg/kg) | $C_{max}{}^a$ (μg eq./mL) | AUC$_{0-\infty}$ (μg eq. hr/mL) | AUC$_{0-\infty}$/Dose (μg eq. hr/mL)/ (mg/kg) | CL (mL/hr/kg) | Vd$_{ss}$ (mL/kg) | t$_{1/2}$ (hr) |
|---|---|---|---|---|---|---|---|
| E06 (anti-HSA)-2V tandem (09_2691) | 0.3 | 4.53 | 47.5 | 158 | 6.32 | 203 | 47.8 |
| H08 (anti-HSA)-2V tandem (09_2992) | 0.3 | 4.81 | 47.9 | 160 | 6.26 | 179 | 39.7 |
| 2V -PEG (09_2313) | 1 | 17.8 | 533 | 533 | 1.89 | 95.8 | 53.5 |
| 2V (08_3952) | 1 | 8.44 | 2.33 | 2.33 | 430 | 869 | 0.146 (~9 min) |

TABLE 6-continued

| Species | Construct | Dose (mg/kg) | Route | Cl (ml/hr/kg) | Vdss (ml/kg) | t½ (h) | F (%) |
|---|---|---|---|---|---|---|---|
| NHP | 2V-E06 | 1 | iv | 0.25 | 75 | 210 | — |
| | E06-2V | 1 | iv | 0.29 | 69 | 164 | — |
| | E06-2V | 0.5 | sc | — | — | * | >75 |

* = Not sufficient data to determine accurate half-life for E06-2V delivered via the subcutaneous route, although data shown graphically to approximate to intravenous dosing half-life.

The half-life of 2V-E06 fusions across all three species in comparison to that of albumin was plotted. Overall these data demonstrate that the half-life values for 2V-E06 lie within 2 fold of those of albumin in all 3 species investigated. However, as all the half-life values obtained for 2V-E06 are similar to those of albumin it is believed that the addition of 2V-E06 has improved the pharmacokinetic of 2V because high affinity binding of the molecule to albumin has led to the 2V-E06 albumin complex taking on the pharmacokinetic and clearance properties of albumin.

Assuming that the 2V-E06 albumin complex takes on the pharmacokinetic properties of albumin, the prediction of the likely pharmacokinetic properties of this molecule in human becomes simply a case of understanding the half-life of albumin in human. Literature data is available for the half-life of albumin in human (19 days). It is therefore anticipated that the half-life of 2V-E06 in human will approximate to 19 days and that it volume of distribution will approximate to 0.1 l/kg (assume volume of distribution is conserved across species).

For each animal model, VNAR concentrations in plasma were analyzed by quantitative LC-MS as described. Briefly, plasma samples were treated as follows: 50 µl plasma was added to 50 µl 6 M guanidine containing the peptide internal standard and reduced with 20 µl of 32 mM Tris (2-carboxyethyl) phosphine-hydrochloride (TCEP) at 56° C. for 45 minutes. Samples were alkylated by addition of 10 µl of 128 mM iodoacetamide at 37° C. for 60 minutes. Samples were diluted by the addition of 150 µl 100 mM phosphate, pH8, 0.1% CHAPS. Using a Kingfisher magnetic bead processor, magnetic Ni-beads (25 µl/sample) were washed in 100 mM phosphate, pH8, 0.1% CHAPS before being transferred to plasma sample plate and incubated for 1 h. Three washes were carried out: 1st and 2nd wash: transfer beads to plate containing 100 µl phosphate, pH8, 0.1% CHAPS; 3rd wash: transfer beads to plate containing 100 µl phosphate, pH8, 0.1% CHAPS+20 mM imidazole. Bound VNAR was then eluted by transferring the beads to a plate containing 100 µl phosphate, pH8, +250 mM imidazole. Beads were removed and 100 µl 100 mM TRIS, pH8 containing 20 µg/ml Trypsin was added and incubated for 4 h at 37° C. Following this, 20 µl 100 mM TRIS, pH8 containing 100 µg/ml Trypsin was added and incubated overnight at 37° C. Samples were then loaded into a CTC PAL auto-sampler and analysed using LC-MS. Signature peptides were separated on an Agilent 1100 HPLC system using an Onyx monolithic RP C18 guard trapping cartridge and a Waters XBridge BEH130 C18 Column, 3.5 µM, 2.1×100 mm analytical column. Peptides were eluted with a gradient of 5% to 45% acetonitrile in water with 0.1% formic acid. Signature peptides within each partner were analysed independently: E06 signature peptide—EQISISGR and 2V signature peptide—AQSLAISTR. The analytes were detected by atmospheric pressure electrospray ionisation MS/MS using an AB Sciex AP15500 QTRAP triple quadrupole mass spectrometer. The ion chromatograms were quantified by reference to standards spiked into fresh control plasma and analysed over the range 0.04 to 50 µg/ml. The ion chromatograms were integrated and quantified by interpolation of the standard curve with a 1/y weighting using AB Sciex Analyst 1.5.1 software.

EXAMPLE 6

Therapeutically Relevant Domains Retain Function when Fused to E06

As 2V had no inherent target antigen or function, it was a good partner for in vivo PK work however to determine the ability of E06 not to inhibit nor impair the function of a fused partner protein, anti-ICOSL VNAR domains (A1 and CC3) in fusion with E06 were studied. Both A1 and CC3 have exhibited efficacy in vitro and in vivo and were good candidates to validate E06's utility as a domain capable of extending the half-life of therapeutically relevant domains.

N, C and N/C terminal fusion of anti-murine ICOSL VNAR (A1 and CC3) and E06 were constructed, expressed, purified and assessed for dual binding against both HSA and mICOSL by BIAcore analyses (Table 7). All constructs were immobilized with HSA on the chip, with flowing over mICOSL. Both dimers and trimers of E06 with A1 and CC3 retained the ability to bind both HSA and ICOSL (A1-Fc average affinity: KD=6.27×10$^{-7}$ M; CC3-Fc average affinity: KD=4.96×10$^{-8}$ M. 2V did not bind ICOSL).

TABLE 7

| Domain | KD (M) |
|---|---|
| A1-E06 | 2.6 × 10$^{-7}$ ± 2.5 × 10$^{-8}$ |
| E06-A1 | 2.1 × 10$^{-7}$ ± 3.43 × 10$^{-8}$ |
| A1-E06-A1 | 4.7 × 10$^{-7}$ ± 9.0 × 10$^{-8}$ |
| CC3-E06 | 7.7 × 10$^{-8}$ ± 1.6 × 10$^{-8}$ |
| E06-CC3 | 1.0 × 10$^{-7}$ ± 1.7 10$^{-8}$ |
| CC3-E06-CC3 | 1.0 × 10$^{-7}$ ± 1.3 × 10$^{-8}$ |
| 2V-E06-2V | — |

To assess the ability of A1 and CC3 to retain the ability to block ligand binding to receptor in cell based neutralization assays, E06 fusions were incorporated (FIG. 6(b)) and the IC$_{50}$ values measured. The assay was carried out follows: CHO cells expressing murine ICOSL receptor were grown to confluency in DMEM/F12+5% FBS media in 96-well cell culture plates (Greiner, Bio-One). mICOSL-hFc (20 µl at 450 ng/ml) was pre-incubated for 1 h with 40 µl of anti-mICOSL-NAR fused to E06 in DMEM/F12+2% FBS and then added to the cells. Following 1 h incubation at 16° C. cells were gently washed 3 times with DMEM/F12+2% FBS and incubated for another 40 min at 16° C. with goat anti-human Fc-HRP (SIGMA) diluted 1:10 000 in the same media. Afterwards the cells were washed again 3 times with DMEM/F12+2% FBS media and ones with PBS and developed with TMB substrate. The results show that single digit nM efficacy was achieved showing the retention of neutralization by both A1 and CC3 when in complex with E06. Results are shown in Table 8 of BIAcore analyses of fusion domains immobilized with HSA and binding mICOSL.

TABLE 8

| Name | Concentration mg/ml | uM | M$_r$ | IC$_{50}$ ng/ml | IC$_{50}$ nm |
|---|---|---|---|---|---|
| A1-E06 | 0.056 | 2.16 | 25.9 | 182.6 | 7.05 |
| E06-A1 | 0.078 | 3.01 | 25.9 | 125.3 | 4.84 |
| A1-E06-A1 | 0.077 | 1.95 | 39.5 | 53.81 | 1.36 |
| CC3-E06 | 0.039 | 1.51 | 25.9 | 61.18 | 2.36 |

TABLE 8-continued

| Name | Concentration mg/ml | uM | $M_r$ | $IC_{50}$ ng/ml | $IC_{50}$ nm |
|---|---|---|---|---|---|
| E06-CC3 | 0.051 | 1.97 | 25.9 | 244 | 9.42 |
| CC3-E06-CC3 | 0.043 | 1.09 | 39.5 | 24.45 | 0.62 |

As a secondary measurement of functionality, T-cell proliferation assays were carried out as follows: antibodies were titrated in 96 well TC flat bottom plate in 100 ul assay media (use the media listed above, but leave out the Rat T stim, IL-2 and IL-1alpha). Tosyl activated magnetic Dynal beads are coated per product insert instructions with hu or mu ICOSL, anti-mu CD3e and hIgG1 filler (1 ug ICOSL/0.5 ug anti-CD3/3.5 ug hIgG1 per 1×10^7 beads). Prior to assay set up, titer beads to determine optimal concentration that gives around 8000-40,000 CPM. Generally for hu ICOSL this will be around 40,000 beads/well and for mu ICOSL, around 20,000 beads/well. Add 50 μl/well of the appropriate beads to the titered antibodies. D10.G4.1 cells are washed 4× with assay media and resuspended to 8×10^5 cells/ml and add 50 μl/well=40,000 cells/well. All wells are brought up to a final volume of 200 μl and incubated for 48 hours. 1 μci/well 3H-thymidine is added and incubated for 5-7 hours. Harvest and count CPM. Both A1 and CC3 still retained the ability to inhibit T cell proliferation when in fusion with E06 as shown in Table 9 and Table 10 with pM $IC_{50}$ values.

TABLE 9

| Sample | $IC_{50}$ nM |
|---|---|
| A1-E06-A1 | 24.02 |
| CC3-E06-CC3 | 5.77 |
| 2V-E06-2V | >128.21 |
| Anti-ICOSL control | 0.04 |

TABLE 10

| Sample | $IC_{50}$ nM |
|---|---|
| A1-hFc | 2.28 |
| CC3-hFC | 0.32 |
| Anti-ICOSL control | 0.03 |
| Rat IgG2A control | — |

The invention claimed is:

1. A fusion protein comprising:

A) a single domain specific binding molecule comprising the Framework Regions FW1, FW2, FW3a, FW3b, and FW4, in which:
  i) FW1 comprises TRVDQSPSSLSASVGDRVTITCVLT (SEQ ID NO: 28), ARVDQSPSSLSASVGDRVTITCVLR (amino acids 1-25 of SEQ ID NO: 67) or TRVDQTPRTATRETGESLTINCVLT (SEQ ID NO: 1),
  ii) FW2 comprises TYWYQQKPGS (SEQ ID NO: 29), TCWYQQKPGK (amino acids 34-43 of SEQ ID NO: 67), or TYWYRKNPGS (SEQ ID NO: 2),
  iii) FW3a comprises GRYSESVN (SEQ ID NO: 30), or GRYVESVN (SEQ ID NO: 3),
  iv) FW3b comprises FTLTISSLQPEDFATYYCRA (SEQ ID NO: 31), FTLTISSLQPEDFATYYCGL (amino acids 65-84 of SEQ ID NO: 67) or FSLRIKDLTVADSATYICRA (SEQ ID NO: 4), and
  v) FW4 comprises GAGTKVEIK (SEQ ID NO: 32), CGQGTKVEIK (amino acids 103-112 of SEQ ID NO: 67) or GAGTVLTVN (SEQ ID NO: 5); or B) a single domain specific binding molecule comprising framework regions FW1, FW2, FW3a, FW3b, and FW4 in which:
  i) FW1 comprises a sequence having at least 50% identity to TRVDQSPSSLSASVGDRVTITCVLT (SEQ ID NO: 28), ARVDQSPSSLSASVGDRVTITCVLR (amino acids 1-25 of SEQ ID NO: 67) or TRVDQTPRTATRETGESLTINCVLT (SEQ ID NO: 1),
  ii) FW2 comprises a sequence having at least 50% identity to TYWYQQKPGS (SEQ ID NO: 29), TCWYQQKPGK (amino acids 34-43 of SEQ ID NO: 67, or TYWYRKNPGS (SEQ ID NO: 2),
  iii) FW3a comprises a sequence having at least 50% identity to GRYSESVN (SEQ ID NO: 30), or GRYVESVN (SEQ ID NO: 3),
  iv) FW3b comprises a sequence having at least 50% identity to FTLTISSLQPEDFATYYCRA (SEQ ID NO: 31), FTLTISSLQPEDFATYYCGL (amino acids 65-84 of SEQ ID NO: 67) or FSLRIKDLTVADSATYICRA (SEQ ID NO: 4), and
  v) FW4 comprises a sequence having at least 50% identity to GAGTKVEIK (SEQ ID NO: 32), CGQGTKVEIK (amino acids 103-112 of SEQ ID NO: 67) or GAGTVLTVN (SEQ ID NO: 5).

2. The fusion protein as claimed in claim 1, which is humanized.

3. The fusion protein of claim 1, wherein the single domain specific binding molecule has an amino acid sequence selected from the group consisting of: E06 (SEQ ID NO. 46), BB11 (SEQ ID NO. 85) and H08 (SEQ ID NO: 36), or a sequence having at least 50% identity thereto.

4. The fusion protein of claim 1, wherein the single domain specific binding molecule has an amino acid sequence selected from the group consisting of: huE06 v1.1 (SEQ ID NO. 68), huH08 v1.1 (SEQ ID NO. 75), huE06 v1.2 (SEQ ID NO. 69), huE06 v1.3 (SEQ ID NO. 70), huE06 v1.4 (SEQ ID NO. 71), huE06 v1.5 (SEQ ID NO. 72), huE06 v1.6 (SEQ ID NO. 76), huE06 v1.7 (SEQ ID NO. 73), huE06 v1.8 (SEQ ID NO. 77), huE06 v1.9 (SEQ ID NO. 78), huE06 v1.10 (SEQ ID NO. 74), AC9 (SEQ ID NO. 79), AD4 (SEQ ID NO. 80), AG11 (SEQ ID NO. 81), AH7 (SEQ ID NO. 82), BA11 (SEQ ID NO. 83), BB10 (SEQ ID NO. 84), BC3 (SEQ ID NO. 86), BD12 (SEQ ID NO. 87), BE4 (SEQ ID NO. 88), or BH4 (SEQ ID NO. 89), or a sequence having at least 50% identity thereto.

5. The fusion protein of claim 1, in which the fusion protein further comprises a biologically active agent fused to the single domain specific binding molecule.

6. The fusion protein of claim 5 wherein the biologically active agent is a pharmaceutically active agent.

7. The fusion protein of claim 5, wherein the biologically active agent is a chemical compound or polymer.

8. The fusion protein as claimed in claim 6, wherein the pharmaceutically active agent is selected from the group consisting of a toxin, anti-inflammatory drug, antibiotic, anti-cancer drug, and analgesic.

9. The fusion protein as claimed in claim 6, wherein the pharmaceutically active agent is a protein.

10. The fusion protein as claimed in claim 9, wherein the protein is an enzyme or fragment thereof, or a cytokine or fragment thereof.

11. The fusion protein as claimed in claim 8, wherein the toxin is cholera toxin or a non-protein toxin.

12. The fusion protein as claimed in claim 8, wherein the anti-inflammatory agent is a non-steroidal anti-inflammatory drug (NSAID) or steroid.

13. The fusion protein as claimed in claim 8, wherein the anti-cancer drug is cytotoxic or cytostatic.

14. The fusion protein as claimed in claim 7, where the chemical compound or polymer is a substance suitable to extend the half-life of the fusion protein in vivo.

15. The fusion protein as claimed in claim 14, wherein the chemical compound or polymer is polyethylene glycol (PEG) and/or cyclodextrin.

16. The fusion protein as claimed in claim 5, wherein the biologically active agent is linked via a linker moiety to the single domain specific binding molecule.

17. The fusion protein as claimed in claim 16, wherein the linker moiety is a peptide, peptide nucleic acid or polyamide linkage.

18. The fusion protein as claimed in claim 5, wherein the single domain specific binding molecule and biologically active agent are joined together by chemical means.

19. The fusion protein as claimed in claim 5, wherein the single domain specific binding molecule and biologically active agent are joined together by peptide bonds through protein synthesis.

20. The fusion protein as claimed in claim 5, wherein the single domain specific binding molecule and biologically active agent are N-, C- and/or N-/C-terminal fusion(s).

21. A nucleic acid encoding the fusion protein of claim 9.

22. A nucleic acid construct comprising a nucleic acid as claimed in claim 21.

23. A host cell comprising a vector as claimed in claim 22.

24. A process for the production of a fusion protein comprising the step of expressing the nucleic acid sequence of claim 21 in a host cell.

25. The process as claimed in claim 24, further comprising the step of purifying the expressed fusion protein.

26. The process as claimed in claim 25, wherein the fusion protein is humanised.

27. A process for the production of a fusion protein of claim 7, wherein the fusion is by chemical means.

28. The process as claimed in claim 27, wherein the chemical means include hydrogen bonds, salt bridges, chemical cross-linking or any combination thereof.

29. A process for the production of a fusion protein comprising the step of expressing the nucleic acid sequence encoding the single domain specific binding molecule of claim 1 in a host cell, and fusing the expressed protein to a chemical compound or polymer.

30. The process as claimed in claim 29, wherein the single domain specific binding molecule is humanised.

31. The process of claim 29, wherein the fusion is chemical synthetic or biosynthetic.

32. The process of claim 31, wherein the biosynthetic fusion is enzymatic.

33. A pharmaceutical composition comprising a fusion protein as claimed in claim 1.

34. The pharmaceutical composition as claimed in claim 33, further comprising at least one of a pharmaceutically acceptable carrier, a pharmaceutically acceptable diluent, a pharmaceutically acceptable adjuvant, and a pharmaceutically acceptable buffer solution.

* * * * *

SEQUENCE LISTING

```
<160> NUMBER OF SEQ ID NOS: 104

<210> SEQ ID NO 1
<211> LENGTH: 25
<212> TYPE: PRT
<213> ORGANISM: Squalus acanthias

<400> SEQUENCE: 1

Thr Arg Val Asp Gln Thr Pro Arg Thr Ala Thr Arg Glu Thr Gly Glu
1               5                   10                  15

Ser Leu Thr Ile Asn Cys Val Leu Thr
            20                  25

<210> SEQ ID NO 2
<211> LENGTH: 10
<212> TYPE: PRT
<213> ORGANISM: Squalus acanthias

<400> SEQUENCE: 2

Thr Tyr Trp Tyr Arg Lys Asn Pro Gly Ser
1               5                   10

<210> SEQ ID NO 3
<211> LENGTH: 8
<212> TYPE: PRT
<213> ORGANISM: Squalus acanthias

<400> SEQUENCE: 3

Gly Arg Tyr Val Glu Ser Val Asn
1               5

<210> SEQ ID NO 4
<211> LENGTH: 20
<212> TYPE: PRT
<213> ORGANISM: Squalus acanthias

<400> SEQUENCE: 4

Phe Ser Leu Arg Ile Lys Asp Leu Thr Val Ala Asp Ser Ala Thr Tyr
1               5                   10                  15
```

Ile Cys Arg Ala
            20

<210> SEQ ID NO 5
<211> LENGTH: 9
<212> TYPE: PRT
<213> ORGANISM: Squalus acanthias

<400> SEQUENCE: 5

Gly Ala Gly Thr Val Leu Thr Val Asn
1               5

<210> SEQ ID NO 6
<211> LENGTH: 8
<212> TYPE: PRT
<213> ORGANISM: Squalus acanthias

<400> SEQUENCE: 6

Asp Thr Ser Tyr Pro Leu Tyr Ser
1               5

<210> SEQ ID NO 7
<211> LENGTH: 9
<212> TYPE: PRT
<213> ORGANISM: Squalus acanthias

<400> SEQUENCE: 7

Met Gly Thr Asn Ile Trp Thr Gly Asp
1               5

<210> SEQ ID NO 8
<211> LENGTH: 9
<212> TYPE: PRT
<213> ORGANISM: Squalus acanthias

<400> SEQUENCE: 8

Met Ala Thr Asn Ile Trp Thr Gly Asp
1               5

<210> SEQ ID NO 9
<211> LENGTH: 9
<212> TYPE: PRT
<213> ORGANISM: Squalus acanthias

<400> SEQUENCE: 9

Met Gly Thr Asp Ser Trp Thr Gly Asp
1               5

<210> SEQ ID NO 10
<211> LENGTH: 9
<212> TYPE: PRT
<213> ORGANISM: Squalus acanthias

<400> SEQUENCE: 10

Met Gly Thr Asn Ser Trp Thr Gly Asp
1               5

<210> SEQ ID NO 11
<211> LENGTH: 9
<212> TYPE: PRT
<213> ORGANISM: Squalus acanthias

<400> SEQUENCE: 11

Met Ser Thr Asn Ile Trp Thr Gly Asp
1               5

```
<210> SEQ ID NO 12
<211> LENGTH: 9
<212> TYPE: PRT
<213> ORGANISM: Squalus acanthias

<400> SEQUENCE: 12

Ile Thr Thr Asp Ser Trp Thr Ser Asp
1               5

<210> SEQ ID NO 13
<211> LENGTH: 9
<212> TYPE: PRT
<213> ORGANISM: Squalus acanthias

<400> SEQUENCE: 13

Met Gly Ala Asn Ser Trp Thr Gly Asp
1               5

<210> SEQ ID NO 14
<211> LENGTH: 9
<212> TYPE: PRT
<213> ORGANISM: Squalus acanthias

<400> SEQUENCE: 14

Met Gly Thr Asn Gly Trp Thr Gly Asp
1               5

<210> SEQ ID NO 15
<211> LENGTH: 9
<212> TYPE: PRT
<213> ORGANISM: Squalus acanthias

<400> SEQUENCE: 15

Ser Asp Ile Ala Met Gly Thr Tyr Asp
1               5

<210> SEQ ID NO 16
<211> LENGTH: 9
<212> TYPE: PRT
<213> ORGANISM: Squalus acanthias

<400> SEQUENCE: 16

Ile Thr Thr His Ser Trp Ser Gly Asp
1               5

<210> SEQ ID NO 17
<211> LENGTH: 9
<212> TYPE: PRT
<213> ORGANISM: Squalus acanthias

<400> SEQUENCE: 17

Leu Ser Thr Tyr Met Glu Ala Gly Asp
1               5

<210> SEQ ID NO 18
<211> LENGTH: 9
<212> TYPE: PRT
<213> ORGANISM: Squalus acanthias

<400> SEQUENCE: 18

Met Asp Thr Ser Ala Gly Val Val Asp
1               5
```

```
<210> SEQ ID NO 19
<211> LENGTH: 19
<212> TYPE: PRT
<213> ORGANISM: Squalus acanthias

<400> SEQUENCE: 19

Glu Ser Pro Pro Ile Cys Thr Ser Gln Gly Ile Ala Ala Val Thr Lys
1               5                   10                  15

Tyr Tyr Asp

<210> SEQ ID NO 20
<211> LENGTH: 10
<212> TYPE: PRT
<213> ORGANISM: Squalus acanthias
<220> FEATURE:
<221> NAME/KEY: SITE
<222> LOCATION: (9)..(9)
<223> OTHER INFORMATION: Xaa represents Gln

<400> SEQUENCE: 20

Tyr Thr Ile His Ile Lys Leu Glu Xaa His
1               5                   10

<210> SEQ ID NO 21
<211> LENGTH: 20
<212> TYPE: PRT
<213> ORGANISM: Squalus acanthias
<220> FEATURE:
<221> NAME/KEY: SITE
<222> LOCATION: (18)..(18)
<223> OTHER INFORMATION: Xaa represents Gln

<400> SEQUENCE: 21

His Ala Gly Tyr Gly Val Trp Asn Arg Gly Leu Gln Trp Arg Gly Tyr
1               5                   10                  15

Asp Xaa Tyr Asp
            20

<210> SEQ ID NO 22
<211> LENGTH: 8
<212> TYPE: PRT
<213> ORGANISM: Squalus acanthias

<400> SEQUENCE: 22

Tyr Thr Pro Gly Arg Glu Asp Tyr
1               5

<210> SEQ ID NO 23
<211> LENGTH: 19
<212> TYPE: PRT
<213> ORGANISM: Squalus acanthias

<400> SEQUENCE: 23

Glu Lys Gly Arg Lys Gly Ser Ala Ile Thr Ser Cys Arg Arg Ser Ser
1               5                   10                  15

Tyr Tyr Asp

<210> SEQ ID NO 24
<211> LENGTH: 13
<212> TYPE: PRT
<213> ORGANISM: Squalus acanthias

<400> SEQUENCE: 24

Gln Ser Leu Ala Ile Ser Thr Arg Ser Tyr Trp Tyr Asp
1               5                   10
```

<210> SEQ ID NO 25
<211> LENGTH: 18
<212> TYPE: PRT
<213> ORGANISM: Squalus acanthias

<400> SEQUENCE: 25

Gly Val Ala Gly Gly Tyr Cys Asp Tyr Ala Leu Cys Ser Ser Arg Tyr
1               5                   10                  15

Ala Glu

<210> SEQ ID NO 26
<211> LENGTH: 9
<212> TYPE: PRT
<213> ORGANISM: Squalus acanthias

<400> SEQUENCE: 26

Ser Asn Lys Glu Gln Ile Ser Ile Ser
1               5

<210> SEQ ID NO 27
<211> LENGTH: 5
<212> TYPE: PRT
<213> ORGANISM: Squalus acanthias

<400> SEQUENCE: 27

Lys Gly Thr Lys Ser
1               5

<210> SEQ ID NO 28
<211> LENGTH: 25
<212> TYPE: PRT
<213> ORGANISM: Artificial sequence
<220> FEATURE:
<223> OTHER INFORMATION: Synthetic sequence: Humanized Framework Region
      FW1

<400> SEQUENCE: 28

Thr Arg Val Asp Gln Ser Pro Ser Ser Leu Ser Ala Ser Val Gly Asp
1               5                   10                  15

Arg Val Thr Ile Thr Cys Val Leu Thr
            20                  25

<210> SEQ ID NO 29
<211> LENGTH: 10
<212> TYPE: PRT
<213> ORGANISM: Artificial sequence
<220> FEATURE:
<223> OTHER INFORMATION: Synthetic sequence: Humanized Framework Region
      FW2

<400> SEQUENCE: 29

Thr Tyr Trp Tyr Gln Gln Lys Pro Gly Ser
1               5                   10

<210> SEQ ID NO 30
<211> LENGTH: 8
<212> TYPE: PRT
<213> ORGANISM: Artificial sequence
<220> FEATURE:
<223> OTHER INFORMATION: Synthetic sequence: Humanized Framework Region
      FW3a

<400> SEQUENCE: 30

Gly Arg Tyr Ser Glu Ser Val Asn

<210> SEQ ID NO 31
<211> LENGTH: 20
<212> TYPE: PRT
<213> ORGANISM: Artificial sequence
<220> FEATURE:
<223> OTHER INFORMATION: Synthetic sequence: Humanized Framework Region FW3b

<400> SEQUENCE: 31

Phe Thr Leu Thr Ile Ser Ser Leu Gln Pro Glu Asp Phe Ala Thr Tyr
1               5                   10                  15

Tyr Cys Arg Ala
            20

<210> SEQ ID NO 32
<211> LENGTH: 9
<212> TYPE: PRT
<213> ORGANISM: Artificial sequence
<220> FEATURE:
<223> OTHER INFORMATION: Synthetic sequence: Humanized Framework Region FW4

<400> SEQUENCE: 32

Gly Ala Gly Thr Lys Val Glu Ile Lys
1               5

<210> SEQ ID NO 33
<211> LENGTH: 103
<212> TYPE: PRT
<213> ORGANISM: Squalus acanthias

<400> SEQUENCE: 33

Ala Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asp Ser Trp Thr Gly Asp Gly Ala
                85                  90                  95

Gly Thr Val Leu Thr Val Asn
            100

<210> SEQ ID NO 34
<211> LENGTH: 103
<212> TYPE: PRT
<213> ORGANISM: Squalus acanthias

<400> SEQUENCE: 34

Ile Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
            50                  55                  60

Ser Phe Ser Leu Arg Ile Lys Asp Leu Thr Val Ala Asp Ser Ala Thr
 65                  70                  75                  80

Tyr Ile Cys Arg Ala Met Gly Thr Asn Ile Trp Thr Gly Asp Gly Ala
                 85                  90                  95

Gly Thr Val Leu Thr Val Asn
            100

<210> SEQ ID NO 35
<211> LENGTH: 103
<212> TYPE: PRT
<213> ORGANISM: Squalus acanthias

<400> SEQUENCE: 35

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Val Glu Ser Val Asn Lys Gly Thr Lys
            50                  55                  60

Ser Phe Ser Leu Arg Ile Lys Asp Leu Thr Val Ala Asp Ser Ala Thr
 65                  70                  75                  80

Tyr Ile Cys Arg Ala Met Gly Thr Asn Ser Trp Thr Gly Asp Gly Ala
                 85                  90                  95

Gly Thr Ala Leu Thr Val Asn
            100

<210> SEQ ID NO 36
<211> LENGTH: 103
<212> TYPE: PRT
<213> ORGANISM: Squalus acanthias

<400> SEQUENCE: 36

Ala Arg Val Asp Gln Thr Pro Arg Thr Ala Thr Lys Glu Thr Gly Glu
 1               5                  10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Val Glu Ser Val Asn Lys Gly Thr Lys
            50                  55                  60

Ser Phe Ser Leu Arg Ile Lys Asp Leu Thr Val Ala Asp Ser Ala Thr
 65                  70                  75                  80

Tyr Ile Cys Arg Ala Met Gly Thr Asn Ile Trp Thr Gly Asp Gly Ala
                 85                  90                  95

Gly Thr Ala Leu Thr Val Asn
            100

<210> SEQ ID NO 37
<211> LENGTH: 103
<212> TYPE: PRT
<213> ORGANISM: Squalus acanthias

<400> SEQUENCE: 37

Thr Arg Val Asp Gln Thr Pro Arg Thr Ala Thr Lys Glu Thr Gly Glu

```
                1               5                  10                 15
Ser Leu Thr Ile Asn Cys Val Leu Thr Asp Thr Ser Tyr Pro Leu Tyr
                20                  25                 30

Ser Thr Tyr Trp Tyr Arg Lys Asn Pro Gly Ser Ser Asn Lys Glu Arg
            35                  40                  45

Ile Ser Ile Ser Gly Arg Tyr Val Glu Ser Val Asn Lys Gly Thr Lys
            50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asx Ser Trp Thr Gly Asp Gly Ala
                85                  90                  95

Gly Thr Val Leu Thr Val Asn
            100
```

<210> SEQ ID NO 38
<211> LENGTH: 103
<212> TYPE: PRT
<213> ORGANISM: Squalus acanthias

<400> SEQUENCE: 38

```
Thr Arg Val Asp Gln Thr Pro Arg Thr Ala Thr Lys Glu Thr Gly Glu
1               5                  10                 15

Ser Leu Thr Ile Asn Cys Val Leu Thr Asp Thr Ser Tyr Pro Leu Tyr
                20                  25                 30

Arg Thr Tyr Trp Tyr Arg Lys Asn Pro Gly Ser Ser Asn Lys Glu Gln
            35                  40                  45

Ile Ser Ile Ser Gly Arg Tyr Val Glu Ser Val Asn Lys Gly Thr Lys
            50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asp Ser Trp Thr Gly Asp Gly Ala
                85                  90                  95

Gly Thr Val Leu Thr Val Asn
            100
```

<210> SEQ ID NO 39
<211> LENGTH: 103
<212> TYPE: PRT
<213> ORGANISM: Squalus acanthias

<400> SEQUENCE: 39

```
Thr Arg Val Asp Gln Thr Pro Arg Thr Ala Thr Lys Glu Thr Gly Glu
1               5                  10                 15

Ser Leu Thr Ile Asn Cys Val Leu Thr Asp Thr Ser Tyr Pro Leu Tyr
                20                  25                 30

Ser Thr Tyr Trp Tyr Arg Lys Asn Pro Gly Ser Ser Asn Lys Glu Arg
            35                  40                  45

Ile Ser Ile Ser Gly Arg Tyr Val Glu Ser Val Asn Lys Gly Thr Lys
            50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asp Ser Trp Thr Gly Asp Gly Ala
                85                  90                  95

Gly Thr Val Leu Thr Val Asn
            100
```

<210> SEQ ID NO 40
<211> LENGTH: 103
<212> TYPE: PRT
<213> ORGANISM: Squalus acanthias

<400> SEQUENCE: 40

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Arg
        35                  40                  45

Ile Ser Ile Ser Gly Arg Tyr Val Glu Ser Val Asn Lys Gly Thr Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asn Ser Trp Thr Gly Asp Gly Ala
                85                  90                  95

Gly Thr Ala Leu Thr Val Asn
            100

<210> SEQ ID NO 41
<211> LENGTH: 103
<212> TYPE: PRT
<213> ORGANISM: Squalus acanthias

<400> SEQUENCE: 41

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asn Ile Trp Thr Gly Asp Gly Ala
                85                  90                  95

Gly Thr Ala Leu Thr Val Asn
            100

<210> SEQ ID NO 42
<211> LENGTH: 103
<212> TYPE: PRT
<213> ORGANISM: Squalus acanthias

<400> SEQUENCE: 42

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
            20                  25                  30

Arg Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asn Ser Trp Thr Gly Asp Gly Ala
                85                  90                  95

Gly Thr Val Leu Thr Val Asn
            100

<210> SEQ ID NO 43
<211> LENGTH: 103
<212> TYPE: PRT
<213> ORGANISM: Squalus acanthias

<400> SEQUENCE: 43

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Arg
            35                  40                  45

Ile Ser Ile Ser Gly Arg Tyr Val Glu Ser Val Asn Lys Gly Thr Lys
        50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asp Ser Trp Thr Gly Asp Gly Ala
                85                  90                  95

Gly Thr Ala Leu Thr Val Asn
            100

<210> SEQ ID NO 44
<211> LENGTH: 103
<212> TYPE: PRT
<213> ORGANISM: Squalus acanthias

<400> SEQUENCE: 44

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Arg
            35                  40                  45

Ile Ser Ile Ser Gly Arg Tyr Val Glu Ser Val Asn Lys Gly Thr Lys
        50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asn Ile Trp Thr Gly Asp Gly Ala
                85                  90                  95

Gly Thr Val Leu Thr Val Asn
            100

<210> SEQ ID NO 45
<211> LENGTH: 103
<212> TYPE: PRT
<213> ORGANISM: Squalus acanthias

<400> SEQUENCE: 45

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
                20                  25                  30

```
Ser Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Met Gly Thr Asn Ile Trp Thr Gly Asp Gly Ala
                85                  90                  95

Gly Thr Val Leu Thr Val Asn
            100

<210> SEQ ID NO 46
<211> LENGTH: 103
<212> TYPE: PRT
<213> ORGANISM: Squalus acanthias

<400> SEQUENCE: 46

Thr Arg Val Asp Gln Thr Pro Arg Thr Ala Thr Arg Glu Thr Gly Glu
 1               5                  10                  15

Ser Leu Thr Ile Asn Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Met Gly Thr Asn Ile Trp Thr Gly Asp Gly Ala
                85                  90                  95

Gly Thr Val Leu Thr Val Asn
            100

<210> SEQ ID NO 47
<211> LENGTH: 103
<212> TYPE: PRT
<213> ORGANISM: Squalus acanthias

<400> SEQUENCE: 47

Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Met Gly Thr Asn Ile Trp Thr Gly Asp Gly Ala
                85                  90                  95

Gly Thr Val Leu Thr Val Asn
            100

<210> SEQ ID NO 48
<211> LENGTH: 103
<212> TYPE: PRT
<213> ORGANISM: Squalus acanthias
```

-continued

<400> SEQUENCE: 48

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Asp Thr Ser Ala Gly Val Val Asp Gly Ala
                85                  90                  95

Gly Thr Val Leu Thr Val Asn
            100

<210> SEQ ID NO 49
<211> LENGTH: 103
<212> TYPE: PRT
<213> ORGANISM: Squalus acanthias

<400> SEQUENCE: 49

Ala Lys Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asp Ser Trp Thr Gly Asp Gly Ala
                85                  90                  95

Gly Thr Val Leu Thr Val Asn
            100

<210> SEQ ID NO 50
<211> LENGTH: 103
<212> TYPE: PRT
<213> ORGANISM: Squalus acanthias

<400> SEQUENCE: 50

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Arg
        35                  40                  45

Ile Ser Ile Ser Gly Arg Tyr Val Glu Ser Val Asn Lys Gly Thr Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asp Ser Trp Thr Gly Asp Gly Ala
                85                  90                  95

Gly Thr Val Leu Thr Val Asn

-continued

```
                100

<210> SEQ ID NO 51
<211> LENGTH: 112
<212> TYPE: PRT
<213> ORGANISM: Artificial sequence
<220> FEATURE:
<223> OTHER INFORMATION: Synthetic sequence: Specific binding domain E06
      with 3xAla - 6xHis tag.

<400> SEQUENCE: 51

Thr Arg Val Asp Gln Thr Pro Arg Thr Ala Thr Arg Glu Thr Gly Glu
1               5                   10                  15

Ser Leu Thr Ile Asn Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asn Ile Trp Thr Gly Asp Gly Ala
                85                  90                  95

Gly Thr Val Leu Thr Val Asn Ala Ala Ala His His His His His His
                100                 105                 110

<210> SEQ ID NO 52
<211> LENGTH: 113
<212> TYPE: PRT
<213> ORGANISM: Squalus acanthias

<400> SEQUENCE: 52

Ile Arg Val Asp Gln Thr Pro Arg Thr Ala Thr Lys Glu Thr Gly Glu
1               5                   10                  15

Ser Leu Thr Ile Asn Cys Val Leu Thr Gly Thr Val Cys Gly Met Tyr
                20                  25                  30

Ser Thr Ser Trp Ser Arg Lys Asn Pro Gly Arg Ala Asp Trp Glu Arg
        35                  40                  45

Ile Ser Ile Gly Gly Arg Tyr Val Glu Ser Val Asn Lys Gly Ala Lys
    50                  55                  60

Ser Phe Ser Leu Arg Ile Arg Asp Leu Thr Val Ala Asp Ser Ala Thr
65                  70                  75                  80

Tyr Cys Cys Ser Ala Glu Ser Pro Pro Ile Cys Thr Ser Gln Gly Ile
                85                  90                  95

Ala Ala Val Thr Lys Tyr Tyr Asp Gly Ala Gly Thr Val Leu Thr Val
                100                 105                 110

Asn

<210> SEQ ID NO 53
<211> LENGTH: 103
<212> TYPE: PRT
<213> ORGANISM: Squalus acanthias

<400> SEQUENCE: 53

Ala Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
                20                  25                  30
```

```
Ser Thr Tyr Trp Tyr Arg Lys Asn Pro Gly Ser Ser Asn Lys Glu Gln
         35                  40                  45

Ile Ser Ile Ser Gly Arg Tyr Val Glu Ser Val Asn Lys Gly Thr Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Ile Thr Thr Asp Ser Trp Thr Ser Asp Gly Ala
                 85                  90                  95

Gly Thr Ala Leu Thr Val Asn
            100
```

<210> SEQ ID NO 54
<211> LENGTH: 104
<212> TYPE: PRT
<213> ORGANISM: Squalus acanthias
<220> FEATURE:
<221> NAME/KEY: SITE
<222> LOCATION: (94)..(94)
<223> OTHER INFORMATION: Xaa represents Gln

<400> SEQUENCE: 54

```
Ala Arg Val Asp Gln Thr Pro Arg Thr Ala Thr Lys Glu Thr Gly Glu
 1               5                  10                  15

Ser Leu Thr Ile Asn Cys Val Leu Thr Asp Thr Ser Tyr Pro Leu Tyr
                 20                  25                  30

Ser Thr Tyr Trp Tyr Arg Lys Asn Pro Gly Ser Ser Asn Lys Glu Gln
         35                  40                  45

Ile Ser Ile Ser Gly Arg Tyr Val Glu Ser Val Asn Lys Gly Thr Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Tyr Thr Ile His Ile Lys Leu Glu Xaa His Gly
                 85                  90                  95

Ala Gly Thr Val Leu Thr Val Asn
            100
```

<210> SEQ ID NO 55
<211> LENGTH: 103
<212> TYPE: PRT
<213> ORGANISM: Squalus acanthias

<400> SEQUENCE: 55

```
Ala Arg Val Asp Gln Thr Pro Arg Thr Ala Thr Lys Glu Thr Gly Glu
 1               5                  10                  15

Ser Leu Thr Ile Asn Cys Val Leu Thr Asp Thr Ser Tyr Pro Leu Tyr
                 20                  25                  30

Ser Thr Tyr Trp Tyr Arg Lys Asn Pro Gly Ser Pro Asn Lys Glu Arg
         35                  40                  45

Ile Ser Ile Ser Gly Arg Tyr Val Glu Ser Val Asn Lys Gly Thr Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Met Gly Ala Asn Ser Trp Thr Gly Asp Gly Ala
                 85                  90                  95

Gly Thr Ala Leu Thr Val Asn
            100
```

<210> SEQ ID NO 56

```
<211> LENGTH: 103
<212> TYPE: PRT
<213> ORGANISM: Squalus acanthias

<400> SEQUENCE: 56

Ala Ser Val Asn Gln Thr Pro Arg Thr Ala Thr Lys Glu Thr Gly Glu
1               5                   10                  15

Ser Leu Thr Ile Asn Cys Val Leu Thr Asp Ala Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Pro Ile Ser Gly Arg Tyr Val Glu Ser Val Asn Lys Gly Thr Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asn Gly Trp Thr Gly Asp Gly Ala
                85                  90                  95

Gly Thr Val Leu Thr Val Asn
            100

<210> SEQ ID NO 57
<211> LENGTH: 114
<212> TYPE: PRT
<213> ORGANISM: Squalus acanthias
<220> FEATURE:
<221> NAME/KEY: SITE
<222> LOCATION: (103)..(103)
<223> OTHER INFORMATION: Xaa represents Gln

<400> SEQUENCE: 57

Ala Lys Val Asp Gln Thr Pro Arg Thr Thr Thr Lys Glu Thr Gly Glu
1               5                   10                  15

Ser Leu Thr Ile Asn Cys Val Leu Thr Glu Thr Ser Tyr Gly Leu Ser
            20                  25                  30

Ser Thr Ser Trp Phe Gln Lys Asn Pro Gly Thr Thr Asp Trp Glu Arg
        35                  40                  45

Met Ser Ile Gly Gly Arg Tyr Val Glu Ser Val Asn Thr Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala His Ala Gly Tyr Gly Val Trp Asn Arg Gly Leu
                85                  90                  95

Gln Trp Arg Gly Tyr Asp Xaa Tyr Asp Gly Ala Gly Thr Val Leu Thr
            100                 105                 110

Val Asn

<210> SEQ ID NO 58
<211> LENGTH: 102
<212> TYPE: PRT
<213> ORGANISM: Squalus acanthias

<400> SEQUENCE: 58

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45
```

```
Ile Ser Ile Ser Gly Arg Tyr Val Glu Ser Val Asn Lys Gly Thr Lys
        50                  55                  60

Ser Phe Ser Leu Arg Ile Lys Asp Leu Thr Val Ala Asp Ser Ala Thr
 65                  70                  75                  80

Tyr Ile Cys Arg Ala Tyr Thr Pro Gly Arg Glu Asp Tyr Gly Ala Gly
                 85                  90                  95

Thr Val Leu Thr Val Asn
            100
```

<210> SEQ ID NO 59
<211> LENGTH: 103
<212> TYPE: PRT
<213> ORGANISM: Squalus acanthias

<400> SEQUENCE: 59

```
Ala Arg Val Asp Gln Thr Pro Arg Thr Ala Thr Lys Glu Thr Gly Glu
 1               5                  10                  15

Ser Leu Thr Ile Asn Cys Val Leu Ala Asp Thr Ser Tyr Pro Leu Tyr
                20                  25                  30

Ser Thr Tyr Trp Tyr Arg Lys Asn Pro Gly Ser Ser Asn Lys Glu Gln
             35                  40                  45

Ile Ser Ile Ser Gly Arg Tyr Val Glu Ser Val Asn Lys Gly Thr Lys
        50                  55                  60

Ser Phe Ser Leu Arg Ile Lys Asp Leu Thr Val Ala Asp Ser Ala Thr
 65                  70                  75                  80

Tyr Ile Cys Arg Ala Ser Asp Ile Ala Met Gly Thr Tyr Asp Gly Ala
                 85                  90                  95

Gly Thr Ala Leu Thr Val Asn
            100
```

<210> SEQ ID NO 60
<211> LENGTH: 113
<212> TYPE: PRT
<213> ORGANISM: Squalus acanthias

<400> SEQUENCE: 60

```
Ala Ser Val Asn Gln Thr Pro Arg Thr Ala Thr Lys Glu Thr Gly Glu
 1               5                  10                  15

Ser Leu Thr Ile Asn Cys Val Leu Thr Gly Thr Ser Cys Ser Leu Tyr
                20                  25                  30

Ser Thr Ser Trp Phe Arg Lys Asn Pro Gly Thr Thr Asp Trp Glu Arg
             35                  40                  45

Ile Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
 65                  70                  75                  80

Tyr Tyr Cys Lys Ala Glu Lys Gly Arg Lys Gly Ser Ala Ile Thr Ser
                 85                  90                  95

Cys Arg Arg Ser Ser Tyr Tyr Asp Gly Ala Gly Thr Val Leu Thr Val
            100                 105                 110

Asn
```

<210> SEQ ID NO 61
<211> LENGTH: 103
<212> TYPE: PRT
<213> ORGANISM: Squalus acanthias

<400> SEQUENCE: 61

```
Ala Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Val Glu Ser Val Asn Lys Gly Thr Lys
        50                  55                  60

Ser Phe Ser Leu Arg Ile Lys Asp Leu Thr Val Ala Asp Ser Gly Thr
65                  70                  75                  80

Tyr Ile Cys Arg Ser Ile Thr Thr His Ser Trp Ser Gly Asp Gly Ala
                85                  90                  95

Gly Thr Ala Leu Thr Val Asn
            100
```

<210> SEQ ID NO 62
<211> LENGTH: 103
<212> TYPE: PRT
<213> ORGANISM: Squalus acanthias

<400> SEQUENCE: 62

```
Ile Arg Val Asp Gln Thr Pro Arg Thr Ala Thr Lys Glu Thr Gly Gly
1               5                   10                  15

Ser Leu Thr Ile Asn Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Val Glu Ser Val Asn Lys Gly Thr Lys
        50                  55                  60

Ser Phe Ser Leu Arg Ile Lys Asp Leu Thr Val Ala Asp Ser Ala Thr
65                  70                  75                  80

Tyr Ile Cys Arg Ala Leu Ser Thr Tyr Met Glu Ala Gly Asp Gly Ala
                85                  90                  95

Gly Thr Val Leu Thr Val Asn
            100
```

<210> SEQ ID NO 63
<211> LENGTH: 103
<212> TYPE: PRT
<213> ORGANISM: Squalus acanthias

<400> SEQUENCE: 63

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Pro Ile Ser Gly Arg Tyr Val Glu Ser Val Asn Lys Gly Thr Lys
        50                  55                  60

Ser Phe Ser Leu Arg Ile Lys Asp Leu Thr Val Ala Asp Ser Ala Thr
65                  70                  75                  80

Tyr Ile Cys Arg Ala Met Asp Thr Ser Ala Gly Val Val Asp Gly Ala
                85                  90                  95

Gly Thr Val Leu Thr Val Asn
            100
```

<210> SEQ ID NO 64
<211> LENGTH: 107
<212> TYPE: PRT
<213> ORGANISM: Squalus acanthias

<400> SEQUENCE: 64

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Leu Ala Ile Ser Thr Arg Ser Tyr Trp
                85                  90                  95

Tyr Asp Gly Ala Gly Thr Val Leu Thr Val Asn
            100                 105

<210> SEQ ID NO 65
<211> LENGTH: 107
<212> TYPE: PRT
<213> ORGANISM: Homo sapiens

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Arg
                85                  90                  95

Thr Phe Gly Gln Gly Thr Lys Val Glu Ile Lys
            100                 105

<210> SEQ ID NO 66
<211> LENGTH: 113
<212> TYPE: PRT
<213> ORGANISM: Ginglymostoma cirratum

<400> SEQUENCE: 66

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Glu Gly Asn Glu Glu Ser
        35                  40                  45

Ile Ser Lys Gly Gly Arg Tyr Val Glu Thr Val Asn Ser Gly Ser Lys
    50                  55                  60

```
Ser Phe Ser Leu Arg Ile Asn Asp Leu Thr Val Glu Asp Gly Gly Thr
 65                  70                  75                  80

Tyr Arg Cys Gly Leu Gly Val Ala Gly Gly Tyr Cys Asp Tyr Ala Leu
                 85                  90                  95

Cys Ser Ser Arg Tyr Ala Glu Cys Gly Asp Gly Thr Ala Val Thr Val
                100                 105                 110

Asn

<210> SEQ ID NO 67
<211> LENGTH: 112
<212> TYPE: PRT
<213> ORGANISM: Artificial sequence
<220> FEATURE:
<223> OTHER INFORMATION: Synthetic sequence: Humanized shark VNAR 5A7
      variant, 5A7 - IVabc

<400> SEQUENCE: 67

Ala Arg Val Asp Gln Ser Pro Ser Ser Leu Ser Ala Ser Val Gly Asp
  1               5                  10                  15

Arg Val Thr Ile Thr Cys Val Leu Arg Asp Ala Ser Tyr Ala Leu Gly
                 20                  25                  30

Ser Thr Cys Trp Tyr Gln Gln Lys Pro Gly Lys Ala Pro Lys Ser Ile
             35                  40                  45

Ser Lys Gly Gly Arg Tyr Ser Glu Ser Val Asn Ser Gly Ser Lys Ser
 50                  55                  60

Phe Thr Leu Thr Ile Ser Ser Leu Gln Pro Glu Asp Phe Ala Thr Tyr
 65                  70                  75                  80

Tyr Cys Gly Leu Gly Val Ala Gly Gly Tyr Cys Asp Tyr Ala Leu Cys
                 85                  90                  95

Ser Ser Arg Tyr Ala Glu Cys Gly Gln Gly Thr Lys Val Glu Ile Lys
                100                 105                 110

<210> SEQ ID NO 68
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 68

Thr Arg Val Asp Gln Ser Pro Ser Ser Leu Ser Ala Ser Val Gly Asp
  1               5                  10                  15

Arg Val Thr Ile Thr Cys Val Leu Thr Asp Thr Ser Tyr Pro Leu Tyr
                 20                  25                  30

Ser Thr Tyr Trp Tyr Gln Gln Lys Pro Gly Ser Ser Asn Lys Glu Gln
             35                  40                  45

Ile Ser Ile Ser Gly Arg Tyr Ser Glu Ser Val Asn Lys Gly Thr Lys
 50                  55                  60

Ser Phe Thr Leu Thr Ile Ser Ser Leu Gln Pro Glu Asp Phe Ala Thr
 65                  70                  75                  80

Tyr Tyr Cys Arg Ala Met Gly Thr Asn Ile Trp Thr Gly Asp Gly Ala
                 85                  90                  95

Gly Thr Lys Val Glu Ile Lys
                100

<210> SEQ ID NO 69
<211> LENGTH: 103
<212> TYPE: PRT
<213> ORGANISM: Artificial sequence
```

<220> FEATURE:
<223> OTHER INFORMATION: Synthetic sequence: Humanized E06 variant

<400> SEQUENCE: 69

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Gln Gln Lys Pro Gly Ser Ser Asn Lys Glu Gln
        35                  40                  45

Ile Ser Ile Ser Gly Arg Tyr Ser Glu Ser Val Asn Ser Gly Ser Lys
    50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 70
<211> LENGTH: 102
<212> TYPE: PRT
<213> ORGANISM: Artificial sequence
<220> FEATURE:
<223> OTHER INFORMATION: Synthetic sequence: Humanized E06 variant

<400> SEQUENCE: 70

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Gln Gln Lys Pro Gly Lys Ala Pro Lys Gln Ile
        35                  40                  45

Ser Ile Ser Gly Arg Tyr Ser Glu Ser Val Asn Ser Gly Ser Lys Ser
    50                  55                  60

Phe Thr Leu Thr Ile Ser Ser Leu Gln Pro Glu Asp Phe Ala Thr Tyr
65                  70                  75                  80

Tyr Cys Arg Ala Met Gly Thr Asn Ile Trp Thr Gly Asp Gly Ala Gly
                85                  90                  95

Thr Lys Val Glu Ile Lys
            100

<210> SEQ ID NO 71
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Val Leu Thr Asp Thr Ser Tyr Pro Leu
            20                  25                  30

Tyr Ser Thr Tyr Trp Tyr Gln Gln Lys Pro Gly Lys Ala Pro Lys Gln
        35                  40                  45

Ile Ser Ile Ser Gly Arg Tyr Ser Glu Ser Val Asn Ser Gly Ser Lys
    50                  55                  60

```
Ser Phe Thr Leu Thr Ile Ser Ser Leu Gln Pro Glu Asp Phe Ala Thr
 65                  70                  75                  80

Tyr Tyr Cys Arg Ala Met Gly Thr Asn Ile Trp Thr Gly Asp Gly Ala
                 85                  90                  95

Gly Thr Lys Val Glu Ile Lys
            100

<210> SEQ ID NO 72
<211> LENGTH: 101
<212> TYPE: PRT
<213> ORGANISM: Artificial sequence
<220> FEATURE:
<223> OTHER INFORMATION: Synthetic sequence: Humanized E06 variant

<400> SEQUENCE: 72

Thr Arg Val Asp Gln Ser Pro Ser Ser Leu Ser Ala Ser Val Gly Asp
  1               5                  10                  15

Arg Val Thr Ile Thr Cys Val Leu Thr Asp Thr Ser Tyr Pro Leu Tyr
                 20                  25                  30

Ser Thr Tyr Trp Tyr Gln Gln Lys Pro Gly Lys Ala Pro Lys Leu Gln
             35                  40                  45

Ile Ser Ile Ser Gly Arg Phe Ser Glu Ser Gly Ser Gly Thr Asp Phe
 50                  55                  60

Thr Leu Thr Ile Ser Ser Leu Gln Pro Glu Asp Phe Ala Thr Tyr Tyr
 65                  70                  75                  80

Cys Arg Ala Met Gly Thr Asn Ile Trp Thr Gly Asp Gly Ala Gly Thr
                 85                  90                  95

Lys Val Glu Ile Lys
            100

<210> SEQ ID NO 73
<211> LENGTH: 102
<212> TYPE: PRT
<213> ORGANISM: Artificial sequence
<220> FEATURE:
<223> OTHER INFORMATION: Synthetic sequence: Humanized E06 variant

<400> SEQUENCE: 73

Thr Arg Val Asp Gln Ser Pro Ser Ser Leu Ser Ala Ser Val Gly Asp
  1               5                  10                  15

Arg Val Thr Ile Thr Cys Val Leu Thr Asp Thr Ser Tyr Pro Leu Tyr
                 20                  25                  30

Ser Thr Tyr Trp Tyr Gln Gln Lys Pro Gly Lys Ala Pro Lys Gln Ile
             35                  40                  45

Ser Ile Ser Gly Arg Tyr Ser Glu Ser Val Asn Lys Gly Thr Lys Ser
 50                  55                  60

Phe Thr Leu Thr Ile Ser Ser Leu Gln Pro Glu Asp Phe Ala Thr Tyr
 65                  70                  75                  80

Tyr Cys Arg Ala Met Gly Thr Asn Ile Trp Thr Gly Asp Gly Ala Gly
                 85                  90                  95

Thr Lys Val Glu Ile Lys
            100

<210> SEQ ID NO 74
<211> LENGTH: 103
<212> TYPE: PRT
<213> ORGANISM: Artificial sequence
<220> FEATURE:
<223> OTHER INFORMATION: Synthetic sequence: Humanized E06 variant
```

-continued

```
<400> SEQUENCE: 74

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 75
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 75

Ala Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Gln Gln Lys Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Ala Leu Thr Val Asn
            100

<210> SEQ ID NO 76
<211> LENGTH: 109
<212> TYPE: PRT
<213> ORGANISM: Artificial sequence
<220> FEATURE:
<223> OTHER INFORMATION: Synthetic sequence: Humanized E06 variant

<400> SEQUENCE: 76

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80
```

Pro Glu Asp Phe Ala Thr Tyr Tyr Cys Arg Ala Met Gly Thr Asn Ile
            85                  90                  95

Trp Thr Gly Asp Gly Ala Gly Thr Lys Val Glu Ile Lys
            100                 105

<210> SEQ ID NO 77
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 77

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Lys Ser Leu Gln Pro Glu Asp Phe Ala Thr
65                  70                  75                  80

Tyr Ile Cys Arg Ala Met Gly Thr Asn Ile Trp Thr Gly Asp Gly Gln
                85                  90                  95

Gly Thr Lys Val Glu Ile Lys
            100

<210> SEQ ID NO 78
<211> LENGTH: 101
<212> TYPE: PRT
<213> ORGANISM: Artificial sequence
<220> FEATURE:
<223> OTHER INFORMATION: Synthetic sequence: Humanized E06 variant

<400> SEQUENCE: 78

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Gly Ser Gly Thr Asp Phe
    50                  55                  60

Thr Leu Thr Ile Lys Ser Leu Gln Pro Glu Asp Phe Ala Thr Tyr Ile
65                  70                  75                  80

Cys Arg Ala Met Gly Thr Asn Ile Trp Thr Gly Asp Gly Gln Gly Thr
                85                  90                  95

Lys Val Glu Ile Lys
            100

<210> SEQ ID NO 79
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 79

Thr Arg Val Asp Gln Ser Pro Ser Ser Leu Ser Ala Ser Val Gly Asp

```
                1               5                   10                  15
            Arg Val Thr Ile Thr Cys Val Leu Thr Asp Thr Ser Tyr Pro Leu Tyr
                            20                  25                  30

Ser Thr Tyr Trp Tyr Arg Lys Asn Pro Gly Ser Ser Asn Lys Glu Gln
                        35                  40                  45

Ile Ser Ile Ser Gly Arg Tyr Ser Glu Ser Val Asn Lys Gly Thr Lys
                    50                  55                  60

Ser Ser Thr Leu Thr Ile Ser Ser Leu Gln Pro Glu Asp Phe Ala Thr
            65                  70                  75                  80

Tyr Tyr Cys Arg Ala Met Gly Thr Asn Ile Trp Thr Gly Asp Gly Ala
                            85                  90                  95

Gly Thr Lys Val Glu Ile Lys
                        100

<210> SEQ ID NO 80
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 80

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Met Ser Gly Arg Tyr Ser Glu Ser Val Asn Lys Ser Thr Lys
        50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 81
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 81

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
        50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95
```

Gly Thr Lys Val Glu Thr Lys
        100

<210> SEQ ID NO 82
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 82

Thr Arg Val Asp Gln Thr Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Ser Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
        100

<210> SEQ ID NO 83
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 83

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys
        100

<210> SEQ ID NO 84
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 84

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr

```
            20                  25                  30
Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
        50                  55                  60

Ser Phe Thr Leu Thr Ile Ser Ser Leu Gln Pro Glu Asp Phe Ala Thr
 65                 70                  75                  80

Tyr Tyr Cys Arg Ala Met Gly Thr Asn Phe Trp Thr Gly Asp Gly Ala
                85                  90                  95

Gly Thr Lys Val Glu Ile Lys
            100

<210> SEQ ID NO 85
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 85

Thr Arg Val Asp Gln Ser Pro Ser Ser Leu Ser Ala Ser Val Gly Asp
 1               5                  10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
        50                  55                  60

Ser Phe Thr Leu Thr Ile Ser Ser Leu Gln Pro Glu Asp Phe Ala Thr
 65                 70                  75                  80

Tyr Tyr Cys Arg Ala Met Ala Thr Asn Ile Trp Thr Gly Asp Gly Ala
                85                  90                  95

Gly Thr Lys Val Glu Ile Lys
            100

<210> SEQ ID NO 86
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 86

Thr Arg Val Asp Gln Ser Pro Ser Ser Leu Ser Ala Ser Val Gly Asp
 1               5                  10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Asn Asn Lys Glu Gln
            35                  40                  45

Ile Ser Ile Ser Gly Arg Tyr Ser Glu Ser Val Asn Lys Gly Thr Lys
        50                  55                  60

Ser Phe Thr Leu Thr Ile Ser Ser Leu Gln Pro Glu Asp Phe Ala Thr
 65                 70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100
```

```
<210> SEQ ID NO 87
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 87

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Asn
    50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 88
<211> LENGTH: 103
<212> TYPE: PRT
<213> ORGANISM: Artificial sequence
<220> FEATURE:
<223> OTHER INFORMATION: Synthetic sequence: Humanized E06 variant

<400> SEQUENCE: 88

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Ser Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 89
<211> LENGTH: 96
<212> TYPE: PRT
<213> ORGANISM: Artificial sequence
<220> FEATURE:
<223> OTHER INFORMATION: Synthetic sequence: Humanized E06 variant

<400> SEQUENCE: 89

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
```

```
                35                  40                  45
Ile Ser Ile Ser Gly Arg Tyr Ser Glu Ser Val Asn Lys Gly Thr Lys
            50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Leu Trp Thr Gly Asp Gly Ala
                85                  90                  95
```

<210> SEQ ID NO 90
<211> LENGTH: 9
<212> TYPE: PRT
<213> ORGANISM: Artificial sequence
<220> FEATURE:
<223> OTHER INFORMATION: Synthetic sequence: Peptide linker

<400> SEQUENCE: 90

```
Ala Ala Ala His His His His His His
1               5
```

<210> SEQ ID NO 91
<211> LENGTH: 8
<212> TYPE: PRT
<213> ORGANISM: Artificial sequence
<220> FEATURE:
<223> OTHER INFORMATION: Synthetic sequence: Humanized Framework Region
      FW2

<400> SEQUENCE: 91

```
Thr Tyr Trp Tyr Gln Gln Lys Pro
1               5
```

<210> SEQ ID NO 92
<211> LENGTH: 7
<212> TYPE: PRT
<213> ORGANISM: Artificial sequence
<220> FEATURE:
<223> OTHER INFORMATION: Synthetic sequence: Humanized Framework Region
      FW3a

<400> SEQUENCE: 92

```
Arg Tyr Ser Glu Ser Val Asn
1               5
```

<210> SEQ ID NO 93
<211> LENGTH: 18
<212> TYPE: PRT
<213> ORGANISM: Artificial sequence
<220> FEATURE:
<223> OTHER INFORMATION: Synthetic sequence: Humanized Framework Region
      FW3b

<400> SEQUENCE: 93

```
Phe Thr Leu Thr Ile Ser Ser Leu Gln Pro Glu Asp Phe Ala Thr Tyr
1               5                   10                  15

Tyr Cys
```

<210> SEQ ID NO 94
<211> LENGTH: 4
<212> TYPE: PRT
<213> ORGANISM: Artificial sequence
<220> FEATURE:
<223> OTHER INFORMATION: Synthetic sequence: Peptide linker

<400> SEQUENCE: 94

```
Gly Gly Gly Gly
```

```
<210> SEQ ID NO 95
<211> LENGTH: 5
<212> TYPE: PRT
<213> ORGANISM: Artificial sequence
<220> FEATURE:
<223> OTHER INFORMATION: Synthetic sequence: Peptide linker

<400> SEQUENCE: 95

Gly Gly Gly Gly Gly
1               5

<210> SEQ ID NO 96
<211> LENGTH: 5
<212> TYPE: PRT
<213> ORGANISM: Artificial sequence
<220> FEATURE:
<223> OTHER INFORMATION: Synthetic sequence: Peptide linker

<400> SEQUENCE: 96

Gly Gly Gly Gly Ser
1               5

<210> SEQ ID NO 97
<211> LENGTH: 9
<212> TYPE: PRT
<213> ORGANISM: Artificial sequence
<220> FEATURE:
<223> OTHER INFORMATION: Synthetic sequence: Peptide linker

<400> SEQUENCE: 97

Gly Gly Gly Gly Ser Gly Gly Gly Gly
1               5

<210> SEQ ID NO 98
<211> LENGTH: 15
<212> TYPE: PRT
<213> ORGANISM: Artificial sequence
<220> FEATURE:
<223> OTHER INFORMATION: Synthetic sequence: Peptide linker

<400> SEQUENCE: 98

Gly Gly Gly Gly Ser Gly Gly Gly Gly Ser Gly Gly Gly Gly Ser
1               5                   10                  15

<210> SEQ ID NO 99
<211> LENGTH: 5
<212> TYPE: PRT
<213> ORGANISM: Squalus acanthias

<400> SEQUENCE: 99

Ser Ser Asn Lys Glu
1               5

<210> SEQ ID NO 100
<211> LENGTH: 4
<212> TYPE: PRT
<213> ORGANISM: Homo sapiens

<400> SEQUENCE: 100

Lys Ala Pro Lys
1

<210> SEQ ID NO 101
<211> LENGTH: 4
```

```
<212> TYPE: PRT
<213> ORGANISM: Squalus acanthias

<400> SEQUENCE: 101

Thr Arg Val Asp
1

<210> SEQ ID NO 102
<211> LENGTH: 5
<212> TYPE: PRT
<213> ORGANISM: Homo sapiens

<400> SEQUENCE: 102

Asp Ile Gln Met Thr
1               5

<210> SEQ ID NO 103
<211> LENGTH: 21
<212> TYPE: PRT
<213> ORGANISM: Squalus acanthias
<220> FEATURE:
<221> NAME/KEY: SITE
<222> LOCATION: (19)..(19)
<223> OTHER INFORMATION: Xaa represents Gln

<400> SEQUENCE: 103

His Ala Gly Tyr Gly Val Trp Asn Arg Gly Leu Gln Trp Arg Gly Tyr
1               5                   10                  15

Asp Asp Xaa Tyr Asp
            20

<210> SEQ ID NO 104
<211> LENGTH: 21
<212> TYPE: PRT
<213> ORGANISM: Squalus acanthias

<400> SEQUENCE: 104

His Ala Gly Tyr Gly Val Trp Asn Arg Gly Leu Gln Trp Arg Gly Tyr
1               5                   10                  15

Asp Asp Tyr Tyr Asp
            20
```